US010667561B2

(12) United States Patent
Verleur et al.

(10) Patent No.: US 10,667,561 B2
(45) Date of Patent: Jun. 2, 2020

(54) VAPORIZER

(71) Applicant: VMR Products LLC., San Francisco, CA (US)

(72) Inventors: Jan Andries Verleur, Miami Beach, FL (US); Dan Recio, Miami, FL (US); Yifeng Lu, Miami, FL (US); Yinjun Zhang, Miami, FL (US); Arturo Fajardo, Miami, FL (US); Hans Verleur, El Dorado, CA (US)

(73) Assignee: VMR Products LLC, San Francisco, CA (US)

( * ) Notice: Subject to any disclaimer, the term of this patent is extended or adjusted under 35 U.S.C. 154(b) by 0 days.

(21) Appl. No.: 16/181,316

(22) Filed: Nov. 5, 2018

(65) Prior Publication Data

US 2019/0069605 A1     Mar. 7, 2019

Related U.S. Application Data

(63) Continuation of application No. 16/119,359, filed on Aug. 31, 2018, which is a continuation of application
(Continued)

(51) Int. Cl.
*A24F 47/00* (2020.01)
*A61M 11/04* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ................. A24F 47/008; A61M 15/06; A61M 2205/332; A61M 2205/82; A61M 11/042; H02J 7/0052

See application file for complete search history.

(56) References Cited

U.S. PATENT DOCUMENTS

| 3,085,145 A | 4/1963 | Wray et al. |
| 3,918,451 A | 11/1975 | Steil et al. |

(Continued)

FOREIGN PATENT DOCUMENTS

| AU | 2014208287 | 12/2016 |
| AU | 2017202891 | 5/2019 |

(Continued)

OTHER PUBLICATIONS

Uptoyou Fromeme, "Newest Elips CCV Pure Flat Shaped Rechargeable Double Electronic Cigarettes E-Cigarette Set",You Tube Video published on Sep. 11, 2013,https://www.youtube.com/watch?v=ZkQe9xztu44 (Year: 2013).*

(Continued)

*Primary Examiner* — Joseph S Del Sole
*Assistant Examiner* — Mohamed K Ahmed Ali
(74) *Attorney, Agent, or Firm* — Mintz Levin Cohn Ferris Glovsky and Popeo, P.C.

(57) ABSTRACT

An electronic cigarette or vaporizer may include a shell and a cartomizer receivable within a chamber within a portion of the shell. A basin may be included in the cartomizer to hold a vaporizable fluid, dry substance, or other vaporizable substance such as a wax. A heating element may be provided within the basin which may have a flexible non-conductive material and a flexible conductive material.

30 Claims, 19 Drawing Sheets

Related U.S. Application Data

No. 14/539,801, filed on Nov. 12, 2014, now Pat. No. 10,085,481.

(60) Provisional application No. 62/015,148, filed on Jun. 20, 2014, provisional application No. 61/937,851, filed on Feb. 10, 2014, provisional application No. 61/903,344, filed on Nov. 12, 2013.

(51) Int. Cl.
A61M 15/06 (2006.01)
H02J 7/00 (2006.01)

(52) U.S. Cl.
CPC .......... *H02J 7/0042* (2013.01); *H02J 7/0052* (2013.01); *A61M 2205/332* (2013.01); *A61M 2205/3368* (2013.01); *A61M 2205/502* (2013.01); *A61M 2205/584* (2013.01); *A61M 2205/8206* (2013.01); *A61M 2205/8237* (2013.01)

(56) References Cited

U.S. PATENT DOCUMENTS

| | | |
|---|---|---|
| 3,934,117 A | 1/1976 | Schladitz et al. |
| 4,171,000 A | 10/1979 | Uhle et al. |
| 4,745,705 A | 5/1988 | Yamamoto |
| 4,793,365 A | 12/1988 | Sensabaugh |
| 4,811,731 A | 3/1989 | Newell |
| 4,941,236 A | 7/1990 | Sherman |
| 4,947,874 A | 8/1990 | Brooks |
| 4,947,875 A | 8/1990 | Brooks |
| 4,993,436 A | 2/1991 | Bloom et al. |
| 5,042,509 A | 8/1991 | Banerjee |
| 5,117,482 A | 5/1992 | Hauber et al. |
| 5,144,962 A | 9/1992 | Counts |
| 5,261,424 A | 11/1993 | Sprinkel et al. |
| 5,269,327 A | 12/1993 | Counts |
| 5,479,948 A | 1/1996 | Counts |
| 5,666,977 A | 9/1997 | Higgins |
| 5,682,050 A | 10/1997 | Williams et al. |
| 5,865,185 A | 2/1999 | Collins |
| 6,090,082 A | 7/2000 | King |
| 6,155,268 A | 12/2000 | Takeuchi et al. |
| 6,443,146 B1 | 9/2002 | Voges et al. |
| 6,516,796 B1 | 2/2003 | Cox |
| 6,532,965 B1 | 3/2003 | Abhulimen |
| 6,708,846 B1 | 3/2004 | Fuchs |
| 6,772,756 B2 | 8/2004 | Shayan et al. |
| 7,173,222 B2 | 2/2007 | Cox |
| 7,318,435 B2 | 1/2008 | Pentafragas et al. |
| D590,990 S | 4/2009 | Hon et al. |
| 7,726,320 B2 | 6/2010 | Robinson |
| 7,802,569 B2 | 9/2010 | Yeates |
| 7,913,688 B2 | 3/2011 | Cross |
| 8,205,622 B2 | 6/2012 | Pan et al. |
| 8,251,060 B2 | 8/2012 | White |
| D675,777 S | 2/2013 | Wu et al. |
| 8,365,742 B2 | 2/2013 | Hon et al. |
| 8,371,310 B2 | 2/2013 | Brenneise et al. |
| D688,415 S | 8/2013 | Kim et al. |
| 8,499,766 B1 | 8/2013 | Newton et al. |
| 8,522,776 B2 | 9/2013 | Wright |
| 8,714,161 B2 | 5/2014 | Liu et al. |
| 8,752,545 B2 | 6/2014 | Buchberger et al. |
| 8,869,792 B1 | 10/2014 | Lee et al. |
| D718,492 S | 11/2014 | Albanese et al. |
| 8,881,737 B2 | 11/2014 | Collett |
| 8,893,726 B2 | 11/2014 | Hon et al. |
| 8,899,240 B2 | 12/2014 | Mass et al. |
| 8,910,639 B2 | 12/2014 | Chang |
| 8,948,578 B2 | 2/2015 | Buchberger et al. |
| 8,978,663 B2 | 3/2015 | Newton et al. |
| 8,991,402 B2 | 3/2015 | Bowen |
| 9,010,335 B1 | 4/2015 | Scatterday et al. |
| 9,055,770 B2 | 6/2015 | Liu et al. |
| 9,072,321 B2 | 7/2015 | Liu et al. |
| 9,072,322 B2 | 7/2015 | Liu et al. |
| 9,078,475 B2 | 7/2015 | Li |
| 9,095,175 B2 | 8/2015 | Terry |
| 9,101,729 B2 | 8/2015 | Liu et al. |
| 9,113,659 B2 | 8/2015 | Liu et al. |
| 9,220,302 B2 | 12/2015 | Depiano |
| D750,320 S | 2/2016 | Verleur |
| 9,247,773 B2 | 2/2016 | Memari |
| 9,254,007 B2 | 2/2016 | Liu et al. |
| D750,835 S | 3/2016 | Wei et al. |
| D752,280 S | 3/2016 | Verleur |
| 9,277,768 B2 | 3/2016 | Xiu et al. |
| 9,289,014 B2 | 3/2016 | Tucker |
| 9,308,336 B2 | 4/2016 | Newton et al. |
| 9,315,890 B1 | 4/2016 | Frick |
| 9,326,547 B2 | 5/2016 | Tucker |
| 9,345,541 B2 | 5/2016 | Greeley |
| 9,364,800 B2 | 6/2016 | Dubief et al. |
| 9,380,812 B2 | 7/2016 | Chung et al. |
| 9,386,805 B2 | 7/2016 | Liu et al. |
| 9,420,829 B2 | 8/2016 | Thorens |
| 9,420,831 B2 | 8/2016 | Liu et al. |
| 9,423,152 B2 | 8/2016 | Ampolini |
| 9,427,022 B2 | 8/2016 | Levin |
| 9,439,456 B2 | 9/2016 | Liu et al. |
| 9,498,588 B2 | 11/2016 | Benassayag |
| 9,504,279 B2 | 11/2016 | Chen et al. |
| 9,516,898 B2 | 12/2016 | Liu et al. |
| 9,532,601 B2 | 1/2017 | Liu et al. |
| 9,555,203 B2 | 1/2017 | Terry |
| 9,578,898 B2 | 2/2017 | Liu et al. |
| 9,591,876 B2 | 3/2017 | Alima et al. |
| 9,603,390 B2 | 3/2017 | Li |
| 9,609,893 B2 | 4/2017 | Novak |
| 9,622,511 B2 | 4/2017 | Zhu et al. |
| 9,629,391 B2 | 4/2017 | Dube |
| 9,629,394 B2 | 4/2017 | Aronie |
| 9,642,397 B2 | 5/2017 | Dai |
| 9,675,117 B2 | 6/2017 | Li |
| 9,687,027 B2 | 6/2017 | Poston |
| 9,687,029 B2 | 6/2017 | Liu et al. |
| 9,717,275 B2 | 8/2017 | Liu et al. |
| 9,717,276 B2 | 8/2017 | Brammer |
| 9,730,471 B2 | 8/2017 | Li |
| 9,738,622 B2 | 8/2017 | Dull |
| 9,743,691 B2 | 8/2017 | Minskoff |
| 9,781,953 B2 | 10/2017 | Verleur |
| 9,795,168 B2 | 10/2017 | Zhu et al. |
| 9,801,413 B2 | 10/2017 | Zhu et al. |
| 9,814,263 B2 | 11/2017 | Cochand |
| 9,814,265 B2 | 11/2017 | Rinker |
| 9,820,508 B2 | 11/2017 | Arnel |
| 9,844,234 B2 | 12/2017 | Thorens |
| 9,861,135 B2 | 1/2018 | Chen et al. |
| 9,918,496 B2 | 3/2018 | Kane |
| 9,974,743 B2 | 5/2018 | Rose |
| 9,986,762 B2 | 6/2018 | Alarcon |
| 9,999,250 B2 | 6/2018 | Minskoff |
| 10,039,321 B2 | 8/2018 | Verleur |
| 10,058,122 B2 | 8/2018 | Steingraber |
| 10,058,124 B2 | 8/2018 | Monsees |
| 10,085,481 B2 | 10/2018 | Verleur |
| 10,111,467 B1 | 10/2018 | Arnel |
| 10,143,233 B2 | 12/2018 | Dubief |
| 10,195,370 B2 | 2/2019 | Chen et al. |
| 2002/0043262 A1 | 4/2002 | Langford |
| 2002/0078951 A1 | 6/2002 | Nichols |
| 2002/0088469 A1 | 7/2002 | Rennecamp et al. |
| 2003/0226837 A1 | 12/2003 | Blake |
| 2004/0050382 A1 | 3/2004 | Goodchild et al. |
| 2005/0016550 A1 | 1/2005 | Katase et al. |
| 2005/0134215 A1 | 6/2005 | Bozzone |
| 2007/0045288 A1 | 3/2007 | Nelson et al. |
| 2007/0074734 A1 | 4/2007 | Braunshteyn |
| 2007/0229025 A1 | 10/2007 | Tsai |
| 2007/0277816 A1 | 12/2007 | Morrison |
| 2007/0283972 A1 | 12/2007 | Monsees |

(56) References Cited

U.S. PATENT DOCUMENTS

| | | |
|---|---|---|
| 2008/0023003 A1 | 1/2008 | Rosenthal et al. |
| 2008/0029095 A1 | 2/2008 | Esser et al. |
| 2008/0257367 A1 | 10/2008 | Paterno |
| 2008/0302374 A1 | 12/2008 | Wengert |
| 2009/0095287 A1 | 4/2009 | Emarlou et al. |
| 2009/0133691 A1 | 5/2009 | Yamada |
| 2009/0272379 A1 | 11/2009 | Thorens |
| 2009/0293892 A1 | 12/2009 | Williams |
| 2009/0302019 A1 | 12/2009 | Selenski |
| 2010/0031968 A1 | 2/2010 | Sheikh |
| 2010/0194337 A1 | 8/2010 | Opolka et al. |
| 2010/0200008 A1 | 8/2010 | Taieb et al. |
| 2010/0207576 A1 | 8/2010 | Elizalde et al. |
| 2010/0253279 A1 | 10/2010 | Matthias et al. |
| 2011/0036346 A1 | 2/2011 | Cohen |
| 2011/0159705 A1 | 6/2011 | Schmidt et al. |
| 2011/0192397 A1 | 8/2011 | Saskar |
| 2011/0226266 A1 | 9/2011 | Tao et al. |
| 2011/0265806 A1 | 11/2011 | Alarcon |
| 2011/0277761 A1 | 11/2011 | Terry |
| 2011/0278189 A1 | 11/2011 | Terry |
| 2011/0303231 A1 | 12/2011 | Li |
| 2012/0018529 A1 | 1/2012 | Gammon |
| 2012/0048266 A1 | 3/2012 | Alelov et al. |
| 2012/0174914 A1 | 7/2012 | Pirshafiey |
| 2012/0199146 A1 | 8/2012 | Marangos et al. |
| 2012/0199663 A1 | 8/2012 | Qiu et al. |
| 2012/0223673 A1 | 9/2012 | Chen |
| 2012/0255546 A1 | 10/2012 | Goetz |
| 2012/0312313 A1 | 12/2012 | Frija et al. |
| 2012/0318882 A1 | 12/2012 | Abehasera et al. |
| 2012/0325227 A1 | 12/2012 | Robinson |
| 2013/0014772 A1 | 1/2013 | Liu et al. |
| 2013/0037041 A1 | 2/2013 | Worm |
| 2013/0042865 A1 | 2/2013 | Monsees |
| 2013/0056013 A1 | 3/2013 | Terry |
| 2013/0081642 A1 | 4/2013 | Safari et al. |
| 2013/0087160 A1 | 4/2013 | Gherghe et al. |
| 2013/0104916 A1 | 5/2013 | Bellinger |
| 2013/0168880 A1 | 7/2013 | Duke et al. |
| 2013/0174842 A1 | 7/2013 | Young |
| 2013/0182421 A1 | 7/2013 | Popper |
| 2013/0192623 A1 | 8/2013 | Tucker |
| 2013/0220315 A1 | 8/2013 | Conley |
| 2013/0228191 A1 | 9/2013 | Newton et al. |
| 2013/0253433 A1 | 9/2013 | Senior |
| 2013/0255675 A1 | 10/2013 | Liu et al. |
| 2013/0255702 A1 | 10/2013 | Griffith |
| 2013/0288081 A1* | 10/2013 | Cheng .................. H01M 2/204 429/7 |
| 2013/0306084 A1 | 11/2013 | Flick et al. |
| 2013/0312742 A1 | 11/2013 | Monsees |
| 2013/0319431 A1 | 12/2013 | Cyphert |
| 2013/0319435 A1 | 12/2013 | Flick et al. |
| 2013/0323941 A1 | 12/2013 | Zeliff |
| 2013/0333711 A1 | 12/2013 | Liu et al. |
| 2014/0000638 A1 | 1/2014 | Sebastian |
| 2014/0014124 A1 | 1/2014 | Glasberg |
| 2014/0041655 A1 | 2/2014 | Barron |
| 2014/0053856 A1 | 2/2014 | Liu et al. |
| 2014/0053857 A1 | 2/2014 | Liu et al. |
| 2014/0053858 A1 | 2/2014 | Liu et al. |
| 2014/0060552 A1 | 3/2014 | Cohen et al. |
| 2014/0060556 A1 | 3/2014 | Liu et al. |
| 2014/0096782 A1 | 4/2014 | Ampolini |
| 2014/0123989 A1 | 5/2014 | Lamothe et al. |
| 2014/0123990 A1 | 5/2014 | Timmermans et al. |
| 2014/0150783 A1 | 6/2014 | Liu et al. |
| 2014/0150784 A1 | 6/2014 | Liu et al. |
| 2014/0150785 A1 | 6/2014 | Malik |
| 2014/0158129 A1 | 6/2014 | Pratt |
| 2014/0166030 A1 | 6/2014 | Li |
| 2014/0174458 A1 | 6/2014 | Katz et al. |
| 2014/0182610 A1 | 7/2014 | Liu et al. |
| 2014/0182612 A1 | 7/2014 | Chen et al. |
| 2014/0190477 A1 | 7/2014 | Qiu et al. |
| 2014/0190496 A1 | 7/2014 | Wensley |
| 2014/0202454 A1 | 7/2014 | Buchberger et al. |
| 2014/0209109 A1 | 7/2014 | Larson et al. |
| 2014/0216484 A1 | 8/2014 | Liu et al. |
| 2014/0224244 A1 | 8/2014 | Liu et al. |
| 2014/0230835 A1 | 8/2014 | Saliman et al. |
| 2014/0253144 A1 | 9/2014 | Novak |
| 2014/0261487 A1 | 9/2014 | Chapman |
| 2014/0261488 A1 | 9/2014 | Tucker et al. |
| 2014/0261490 A1 | 9/2014 | Kane et al. |
| 2014/0261492 A1 | 9/2014 | Kane |
| 2014/0261493 A1 | 9/2014 | Smith |
| 2014/0270729 A1 | 9/2014 | Depiano |
| 2014/0270730 A1 | 9/2014 | Depiano |
| 2014/0283823 A1 | 9/2014 | Liu et al. |
| 2014/0283858 A1 | 9/2014 | Liu et al. |
| 2014/0283859 A1 | 9/2014 | Minskoff |
| 2014/0290677 A1 | 10/2014 | Liu et al. |
| 2014/0299137 A1 | 10/2014 | Kieckbusch |
| 2014/0299141 A1 | 10/2014 | Flick et al. |
| 2014/0311503 A1 | 10/2014 | Liu et al. |
| 2014/0332020 A1 | 11/2014 | Li |
| 2014/0332022 A1 | 11/2014 | Li |
| 2014/0334802 A1 | 11/2014 | Dubief et al. |
| 2014/0334803 A1 | 11/2014 | Li |
| 2014/0334804 A1 | 11/2014 | Choi et al. |
| 2014/0338685 A1 | 11/2014 | Amir et al. |
| 2014/0345631 A1 | 11/2014 | Bowen |
| 2014/0353856 A1 | 12/2014 | Dubief et al. |
| 2014/0355969 A1 | 12/2014 | Stern et al. |
| 2014/0360516 A1 | 12/2014 | Liu et al. |
| 2014/0366898 A1 | 12/2014 | Monsees |
| 2014/0373833 A1 | 12/2014 | Liu et al. |
| 2014/0376895 A1 | 12/2014 | Han et al. |
| 2015/0007836 A1 | 1/2015 | Li |
| 2015/0013695 A1 | 1/2015 | Mcneal |
| 2015/0020825 A1 | 1/2015 | Galloway |
| 2015/0020831 A1 | 1/2015 | Weigensberg |
| 2015/0027457 A1 | 1/2015 | Janardhan |
| 2015/0027460 A1 | 1/2015 | Liu et al. |
| 2015/0027471 A1 | 1/2015 | Feldman |
| 2015/0034103 A1 | 2/2015 | Hon et al. |
| 2015/0034104 A1 | 2/2015 | Zhou et al. |
| 2015/0040929 A1 | 2/2015 | Hon et al. |
| 2015/0047658 A1 | 2/2015 | Cyphert |
| 2015/0053220 A1 | 2/2015 | Levy |
| 2015/0059783 A1 | 3/2015 | Liu et al. |
| 2015/0059787 A1 | 3/2015 | Qiu et al. |
| 2015/0083147 A1 | 3/2015 | Schiff |
| 2015/0090253 A1 | 4/2015 | Farrow et al. |
| 2015/0090256 A1 | 4/2015 | Chung et al. |
| 2015/0090278 A1 | 4/2015 | Schiff |
| 2015/0090281 A1 | 4/2015 | Chen et al. |
| 2015/0101625 A1 | 4/2015 | Newton |
| 2015/0101626 A1 | 4/2015 | Li |
| 2015/0118895 A1 | 4/2015 | Zheng |
| 2015/0128967 A1 | 5/2015 | Robinson |
| 2015/0128977 A1 | 5/2015 | Li |
| 2015/0136158 A1 | 5/2015 | Stevens |
| 2015/0144145 A1 | 5/2015 | Chang |
| 2015/0144147 A1 | 5/2015 | Li |
| 2015/0150305 A1 | 6/2015 | Shenkal et al. |
| 2015/0150307 A1 | 6/2015 | Liu et al. |
| 2015/0157055 A1* | 6/2015 | Lord .................... A24F 47/008 131/329 |
| 2015/0164138 A1 | 6/2015 | Liu et al. |
| 2015/0164141 A1 | 6/2015 | Newton et al. |
| 2015/0164146 A1 | 6/2015 | Li |
| 2015/0164147 A1 | 6/2015 | Verleur |
| 2015/0173422 A1 | 6/2015 | Liu et al. |
| 2015/0181940 A1 | 7/2015 | Liu et al. |
| 2015/0181943 A1 | 7/2015 | Li |
| 2015/0181944 A1 | 7/2015 | Li |
| 2015/0189918 A1 | 7/2015 | Liu et al. |
| 2015/0189919 A1 | 7/2015 | Liu et al. |
| 2015/0201674 A1 | 7/2015 | Dooly |
| 2015/0208728 A1 | 7/2015 | Lord et al. |
| 2015/0208730 A1 | 7/2015 | Li |

(56) References Cited

U.S. PATENT DOCUMENTS

| | | |
|---|---|---|
| 2015/0216234 A1 | 8/2015 | Chung et al. |
| 2015/0216237 A1 | 8/2015 | Wensley |
| 2015/0217068 A1 | 8/2015 | Wakalopulos et al. |
| 2015/0223521 A1 | 8/2015 | Menting |
| 2015/0223522 A1 | 8/2015 | Ampolini |
| 2015/0223523 A1 | 8/2015 | Mccullough et al. |
| 2015/0224268 A1 | 8/2015 | Henry |
| 2015/0245659 A1 | 9/2015 | Depiano |
| 2015/0245661 A1 | 9/2015 | Milin et al. |
| 2015/0245669 A1 | 9/2015 | Cadieux |
| 2015/0257441 A1 | 9/2015 | Gerkin et al. |
| 2015/0257444 A1 | 9/2015 | Chung et al. |
| 2015/0257445 A1 | 9/2015 | Henry |
| 2015/0257447 A1 | 9/2015 | Sullivan et al. |
| 2015/0258289 A1 | 9/2015 | Henry |
| 2015/0272217 A1 | 10/2015 | Chen et al. |
| 2015/0282525 A1 | 10/2015 | Plojoux |
| 2015/0282526 A1 | 10/2015 | Wu et al. |
| 2015/0282529 A1 | 10/2015 | Li |
| 2015/0282530 A1 | 10/2015 | Johnson |
| 2015/0289565 A1 | 10/2015 | Cadieux |
| 2015/0296885 A1 | 10/2015 | Liu et al. |
| 2015/0296888 A1 | 10/2015 | Liu et al. |
| 2015/0296889 A1 | 10/2015 | Liu et al. |
| 2015/0305407 A1 | 10/2015 | Li |
| 2015/0305409 A1 | 10/2015 | Verleur |
| 2015/0313282 A1 | 11/2015 | Ademe |
| 2015/0313283 A1 | 11/2015 | Collett |
| 2015/0320116 A1 | 11/2015 | Bleloch |
| 2015/0327596 A1 | 11/2015 | Alarcon |
| 2015/0333552 A1 | 11/2015 | Alarcon et al. |
| 2015/0333561 A1 | 11/2015 | Alarcon et al. |
| 2015/0335071 A1 | 11/2015 | Brinkley |
| 2015/0335075 A1 | 11/2015 | Minskoff |
| 2015/0342255 A1 | 12/2015 | Wu et al. |
| 2015/0351454 A1 | 12/2015 | Huang et al. |
| 2015/0351455 A1 | 12/2015 | Liu et al. |
| 2015/0351456 A1 | 12/2015 | Johnson |
| 2015/0357608 A1 | 12/2015 | Huang et al. |
| 2016/0000147 A1 | 1/2016 | Li |
| 2016/0007653 A1 | 1/2016 | Tu et al. |
| 2016/0015082 A1 | 1/2016 | Liu et al. |
| 2016/0021933 A1 | 1/2016 | Thorens |
| 2016/0029697 A1 | 2/2016 | Shafer et al. |
| 2016/0029699 A1 | 2/2016 | Li |
| 2016/0044962 A1 | 2/2016 | Thorens |
| 2016/0044965 A1 | 2/2016 | Liu et al. |
| 2016/0044966 A1 | 2/2016 | Li |
| 2016/0051716 A1 | 2/2016 | Wheelock et al. |
| 2016/0057811 A1 | 2/2016 | Alarcon |
| 2016/0058074 A1 | 3/2016 | Liu et al. |
| 2016/0073690 A1 | 3/2016 | Liu et al. |
| 2016/0073694 A1 | 3/2016 | Liu et al. |
| 2016/0081395 A1 | 3/2016 | Thorens |
| 2016/0095352 A1 | 4/2016 | Liu et al. |
| 2016/0106936 A1 | 4/2016 | Kimmel et al. |
| 2016/0113326 A1 | 4/2016 | Li |
| 2016/0120226 A1 | 5/2016 | Rado et al. |
| 2016/0128384 A1 | 5/2016 | Luciani et al. |
| 2016/0128388 A1 | 5/2016 | Liu et al. |
| 2016/0143365 A1 | 5/2016 | Liu et al. |
| 2016/0150824 A1 | 6/2016 | Memari |
| 2016/0157523 A1 | 6/2016 | Liu et al. |
| 2016/0198767 A1 | 7/2016 | Verleur et al. |
| 2016/0198768 A1 | 7/2016 | Liu et al. |
| 2016/0198770 A1 | 7/2016 | Alarcon et al. |
| 2016/0205999 A1 | 7/2016 | Liu et al. |
| 2016/0219938 A1 | 8/2016 | Mamoun |
| 2016/0242466 A1 | 8/2016 | Lord |
| 2016/0249682 A1 | 9/2016 | Leadley |
| 2016/0270442 A1 | 9/2016 | Liu et al. |
| 2016/0270446 A1 | 9/2016 | Shenkal |
| 2016/0278435 A1 | 9/2016 | Choukroun |
| 2016/0278436 A1 | 9/2016 | Verleur |
| 2016/0302471 A1 | 10/2016 | Bowen |
| 2016/0302485 A1 | 10/2016 | Alima et al. |
| 2016/0302486 A1 | 10/2016 | Eroch et al. |
| 2016/0309779 A1 | 10/2016 | Liu et al. |
| 2016/0309789 A1 | 10/2016 | Thomas et al. |
| 2016/0338411 A1 | 11/2016 | Liu et al. |
| 2016/0345628 A1 | 12/2016 | Sabet et al. |
| 2016/0353804 A1 | 12/2016 | Lord et al. |
| 2016/0360784 A1 | 12/2016 | Liu et al. |
| 2016/0374393 A1 | 12/2016 | Chen et al. |
| 2017/0006916 A1 | 1/2017 | Liu et al. |
| 2017/0013875 A1 | 1/2017 | Schennum |
| 2017/0013876 A1 | 1/2017 | Schennum |
| 2017/0013882 A1 | 1/2017 | Liu et al. |
| 2017/0027221 A1 | 2/2017 | Liu et al. |
| 2017/0035109 A1 | 2/2017 | Liu et al. |
| 2017/0042229 A1 | 2/2017 | Liu et al. |
| 2017/0042242 A1 | 2/2017 | Hon et al. |
| 2017/0042248 A1 | 2/2017 | Xiang et al. |
| 2017/0049149 A1 | 2/2017 | Carty et al. |
| 2017/0049152 A1 | 2/2017 | Liu et al. |
| 2017/0071251 A1 | 3/2017 | Goch et al. |
| 2017/0071256 A1 | 3/2017 | Verleur |
| 2017/0086501 A1 | 3/2017 | Buehler |
| 2017/0099880 A1 | 4/2017 | Hawes et al. |
| 2017/0135401 A1 | 5/2017 | Dickens et al. |
| 2017/0143038 A1 | 5/2017 | Dickens et al. |
| 2017/0143040 A1 | 5/2017 | Liu et al. |
| 2017/0157341 A1 | 6/2017 | Pandya |
| 2017/0164655 A1 | 6/2017 | Chen et al. |
| 2017/0197046 A1 | 7/2017 | Buchberger et al. |
| 2017/0202267 A1 | 7/2017 | Liu et al. |
| 2017/0207499 A1 | 7/2017 | Leadley et al. |
| 2017/0208865 A1 | 7/2017 | Nettenstrom |
| 2017/0208866 A1 | 7/2017 | Liu et al. |
| 2017/0208870 A1 | 7/2017 | Liu et al. |
| 2017/0214261 A1 | 7/2017 | Gratton et al. |
| 2017/0215476 A1 | 8/2017 | Dickens |
| 2017/0222468 A1 | 8/2017 | Schennum |
| 2017/0224014 A1 | 8/2017 | Fraser et al. |
| 2017/0231284 A1 | 8/2017 | Newns et al. |
| 2017/0238611 A1 | 8/2017 | Buchberger et al. |
| 2017/0245554 A1 | 8/2017 | Perez |
| 2017/0246405 A1 | 8/2017 | Wensley |
| 2017/0251725 A1 | 9/2017 | Buchberger |
| 2017/0273359 A1 | 9/2017 | Liu et al. |
| 2017/0295847 A1 | 10/2017 | Liu et al. |
| 2017/0325504 A1 | 11/2017 | Liu et al. |
| 2017/0347706 A1 | 12/2017 | Aoun |
| 2018/0303169 A1* | 10/2018 | Sears ............... A24F 47/008 |

FOREIGN PATENT DOCUMENTS

| | | |
|---|---|---|
| CA | 2641869 | 5/2010 |
| CN | 201104488 | 8/2008 |
| CN | 201408820 | 2/2010 |
| CN | 201430916 | 3/2010 |
| CN | 101869356 | 10/2010 |
| CN | 201781984 | 4/2011 |
| CN | 202004499 | 10/2011 |
| CN | 202566289 | 12/2012 |
| CN | 202603608 | 12/2012 |
| CN | 202890462 | 4/2013 |
| CN | 202941411 | 5/2013 |
| CN | 203040683 | 7/2013 |
| CN | 203087525 | 7/2013 |
| CN | 203152489 | 8/2013 |
| CN | 203182012 | 9/2013 |
| CN | 203182014 U | 9/2013 |
| CN | 102727969 | 2/2014 |
| CN | 203467677 | 3/2014 |
| CN | 203538385 | 4/2014 |
| CN | 204070533 | 1/2015 |
| CN | 204120231 | 1/2015 |
| CN | 204180941 | 3/2015 |
| CN | 204217907 | 3/2015 |
| DE | 19619536 | 10/1997 |
| DE | 102006004484 | 8/2007 |
| DE | 202012004792 U1 | 6/2012 |
| EP | 0358114 | 3/1990 |

(56) References Cited

FOREIGN PATENT DOCUMENTS

| | | |
|---|---|---|
| EP | 0845220 | 9/2003 |
| EP | 2399636 | 12/2011 |
| EP | 2614731 | 7/2013 |
| EP | 2967154 | 10/2018 |
| GB | 2264237 | 8/1993 |
| GB | 2266466 | 11/1993 |
| KR | 101011453 | 1/2011 |
| KR | 20110006928 U | 7/2011 |
| KR | 200457340 Y1 | 12/2011 |
| KR | 20120008751 | 2/2012 |
| KR | 20120113519 | 10/2012 |
| KR | 20130106741 | 9/2013 |
| KR | 20130107658 | 10/2013 |
| WO | WO03061716 | 7/2003 |
| WO | WO2003103387 | 12/2003 |
| WO | WO2004080216 | 9/2004 |
| WO | WO2008077271 | 7/2008 |
| WO | WO2010118644 | 10/2010 |
| WO | WO2011125058 | 10/2011 |
| WO | WO2012059726 | 5/2012 |
| WO | WO2012062600 | 5/2012 |
| WO | WO2013020220 | 2/2013 |
| WO | WO2013040193 | 3/2013 |
| WO | WO2013044537 | 4/2013 |
| WO | WO2013068100 | 5/2013 |
| WO | WO2013076750 | 5/2013 |
| WO | WO2013083635 | 6/2013 |
| WO | WO2013089358 | 6/2013 |
| WO | WO2013098397 | 7/2013 |
| WO | WO2013110208 | 8/2013 |
| WO | WO2013110209 | 8/2013 |
| WO | WO2013110210 | 8/2013 |
| WO | WO2013113173 | 8/2013 |
| WO | WO2013113174 | 8/2013 |
| WO | WO2013116983 | 8/2013 |
| WO | WO2013171206 | 11/2013 |
| WO | WO2013174001 | 11/2013 |
| WO | WO2014047948 | 4/2014 |
| WO | WO2014101401 | 7/2014 |
| WO | WO2014101734 | 7/2014 |
| WO | WO2014110750 | 7/2014 |
| WO | WO2014121509 | 8/2014 |
| WO | WO2014127446 | 8/2014 |
| WO | WO2014150979 | 9/2014 |
| WO | WO2014161181 | 10/2014 |
| WO | WO2014169667 | 10/2014 |
| WO | WO2015024239 | 2/2015 |
| WO | WO2015027383 | 3/2015 |
| WO | WO2015027435 | 3/2015 |
| WO | WO2015027470 | 3/2015 |
| WO | WO2015032093 | 3/2015 |
| WO | WO2015037925 | 3/2015 |
| WO | WO2015051538 | 4/2015 |
| WO | WO2015054862 | 4/2015 |
| WO | WO2015066136 | 5/2015 |
| WO | WO2015066927 | 5/2015 |
| WO | WO2015070398 | 5/2015 |
| WO | WO2015070405 | 5/2015 |
| WO | WO2015071703 | 5/2015 |
| WO | WO2015074187 | 5/2015 |
| WO | WO2015074265 | 5/2015 |
| WO | WO2015077645 | 5/2015 |
| WO | WO2015079197 | 6/2015 |
| WO | WO2015082560 | 6/2015 |
| WO | WO2015109476 | 7/2015 |
| WO | WO2015114325 | 8/2015 |
| WO | WO2015120588 | 8/2015 |
| WO | WO2015120623 | 8/2015 |
| WO | WO2015123831 | 8/2015 |
| WO | WO2015143648 | 10/2015 |
| WO | WO2015149330 | 10/2015 |
| WO | WO2015149332 | 10/2015 |
| WO | WO2015149406 | 10/2015 |
| WO | WO2015154309 | 10/2015 |
| WO | WO2015157891 | 10/2015 |
| WO | WO2015157893 | 10/2015 |
| WO | WO2015157900 | 10/2015 |
| WO | WO2015158548 | 10/2015 |
| WO | WO2015161406 | 10/2015 |
| WO | WO2015161553 | 10/2015 |
| WO | WO2015165081 | 11/2015 |
| WO | WO2015165086 | 11/2015 |
| WO | WO2015165105 | 11/2015 |
| WO | WO2015168912 | 11/2015 |
| WO | WO2015176230 | 11/2015 |
| WO | WO2015176300 | 11/2015 |
| WO | WO2015176580 | 11/2015 |
| WO | WO2015180071 | 12/2015 |
| WO | WO2015180088 | 12/2015 |
| WO | WO2015184620 | 12/2015 |
| WO | WO2015184747 | 12/2015 |
| WO | WO2015190810 | 12/2015 |
| WO | WO2015192326 | 12/2015 |
| WO | WO2015196332 | 12/2015 |
| WO | WO2016000130 | 1/2016 |
| WO | WO2016000136 | 1/2016 |
| WO | WO2016000206 | 1/2016 |
| WO | WO2016000232 | 1/2016 |
| WO | WO2016000233 | 1/2016 |
| WO | WO2016015246 | 2/2016 |
| WO | WO2016019353 | 2/2016 |
| WO | WO2016023173 | 2/2016 |
| WO | WO2016023212 | 2/2016 |
| WO | WO2016026104 | 2/2016 |
| WO | WO2016026105 | 2/2016 |
| WO | WO2016026156 | 2/2016 |
| WO | WO2016029567 | 3/2016 |
| WO | WO2016033721 | 3/2016 |
| WO | WO2016041114 | 3/2016 |
| WO | WO2016041140 | 3/2016 |
| WO | WO2016041141 | 3/2016 |
| WO | WO2016041207 | 3/2016 |
| WO | WO2016041209 | 3/2016 |
| WO | WO2016045058 | 3/2016 |
| WO | WO2016049822 | 4/2016 |
| WO | WO2016049823 | 4/2016 |
| WO | WO2016049855 | 4/2016 |
| WO | WO2016054793 | 4/2016 |
| WO | WO2016058139 | 4/2016 |
| WO | WO2016059000 | 4/2016 |
| WO | WO2016061730 | 4/2016 |
| WO | WO2016061822 | 4/2016 |
| WO | WO2016062168 | 4/2016 |
| WO | WO2016065521 | 5/2016 |
| WO | WO2016065532 | 5/2016 |
| WO | WO2016065533 | 5/2016 |
| WO | WO2016065596 | 5/2016 |
| WO | WO2016065598 | 5/2016 |
| WO | WO2016065599 | 5/2016 |
| WO | WO2016070553 | 5/2016 |

OTHER PUBLICATIONS

"New Tank E-Cigarette:innokin 510T." From China Manufacturer, Manufactory, Factory and Supplier on ECVV.com, Nov. 15, 2011, www.ecvv.com/product/3118191.html.

Chinabuye. "Innokin ITaste VV Tank Starter Kit Electronic Cigarette with Clearomizer." YouTube, YouTube, Jul. 23, 2013, www.youtube.com/watch?v=mz414d8MU20.

Cloud pen vaporizer unboxing review by vaporizer blog // VaporizerBlog.com, https://www.youtube.com/watch?v=ixHMkXoWKNg.

Glory Vapes. "Glory Vapes TV: Kanger S1 Cubica Series Starter Kit Unboxing." YouTube, YouTube, Aug. 8, 2013, www.youtube.com/watch?v=NQivJ6YhdbA.

Joye eGo-Tank System XXL 1000mAh Starter Kit, https://www.myvaporstore.com/eGo-Tank-System-XXL-1000rnAh-Starter-Kit-p/ego-t-xxlkit.htm.

Uptoyou Fromeme. "Newest Elips CCV Pure Flat Shaped Rechargeable Double Electronic Cigarettes E-Cigarette Set." YouTube, Sep. 11, 2013, https://www.youtube.com/watch?v=ZkQe9xztu44.

Uptoyou Fromeme. "Elips Ego SOLE Electronic Cigarette Kit

(56) References Cited

OTHER PUBLICATIONS

Patent Elipse Flat Upgrade F6 Section with Atomizer CE4." YouTube, YouTube, Sep. 12, 2013, www.youtube.corn/watch?v=cnPcqDzFm0Q.

Vaporizers Reviewed. "AtmosRX Optimus 510 Vaporizer Review." YouTube, YouTube, Oct. 10, 2013, www.youtube.com/watch?v=wsyQncG8FB8.

Vaporizers Reviewed. "MicroG Pen Vaporizer Review." YouTube, YouTube, Nov. 6, 2013, www.youtube.corn/watch?v=pLhtL8vosrs.

\* cited by examiner

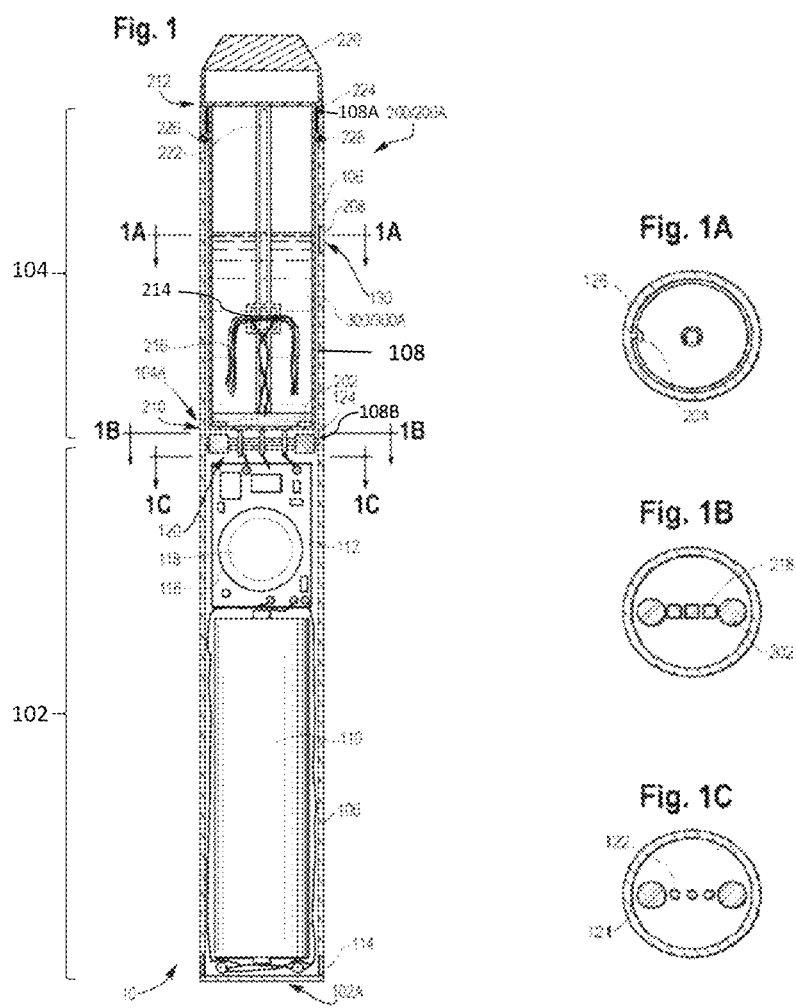

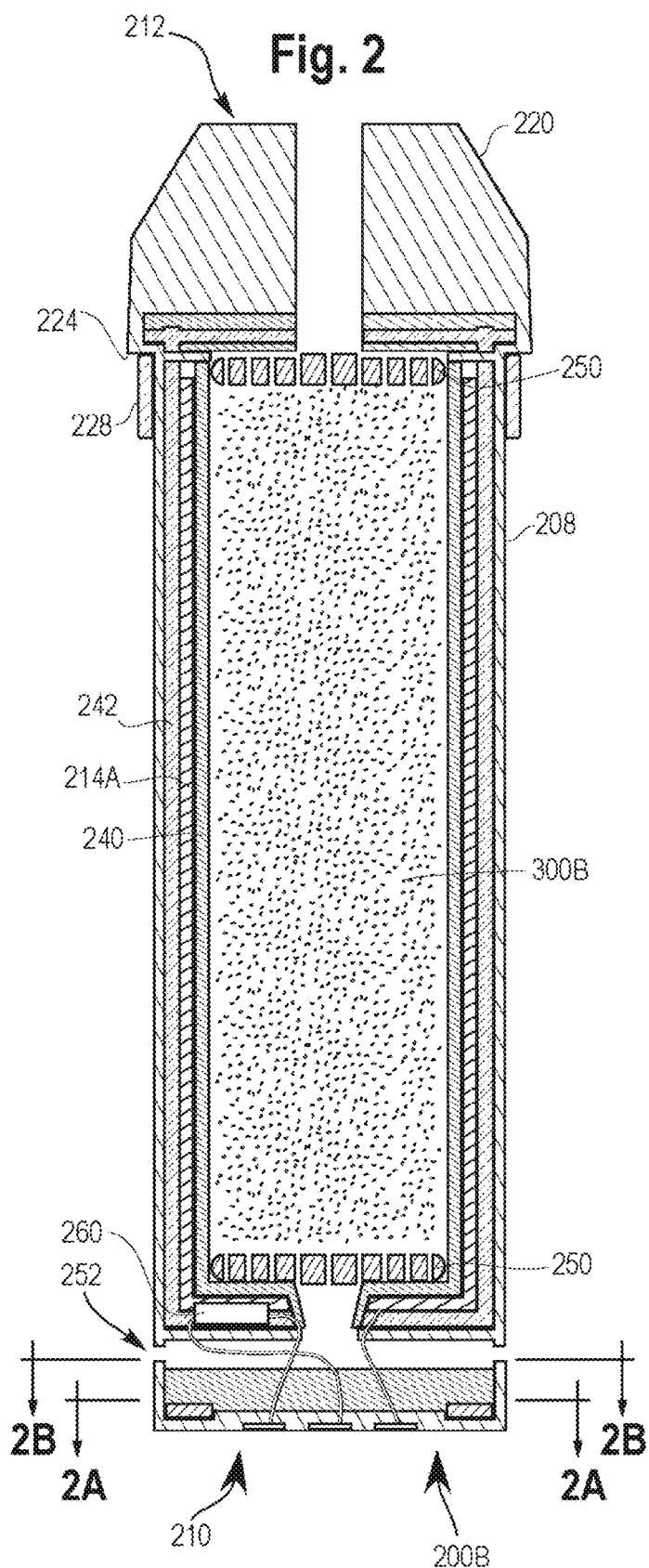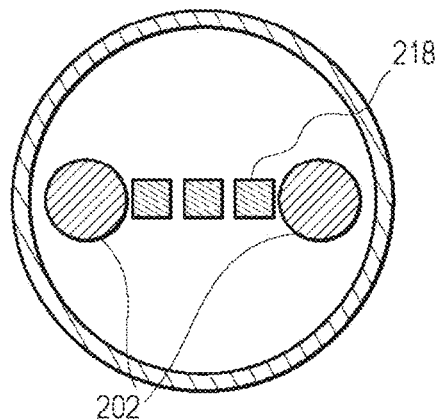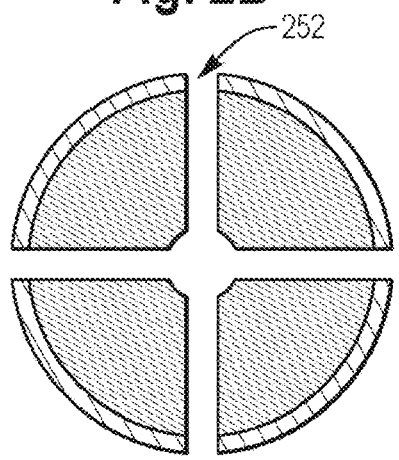

Fig. 13
Fig. 14
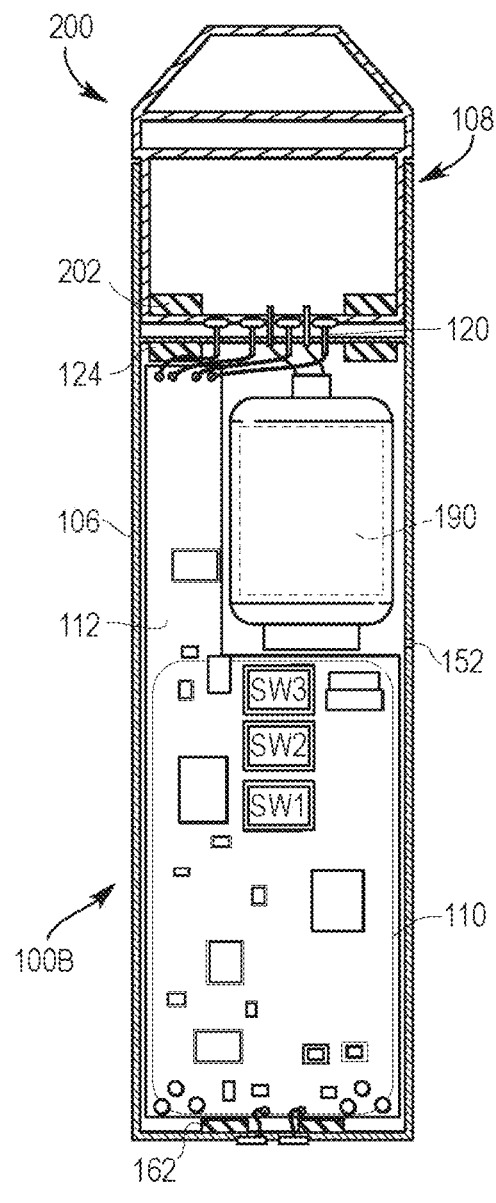
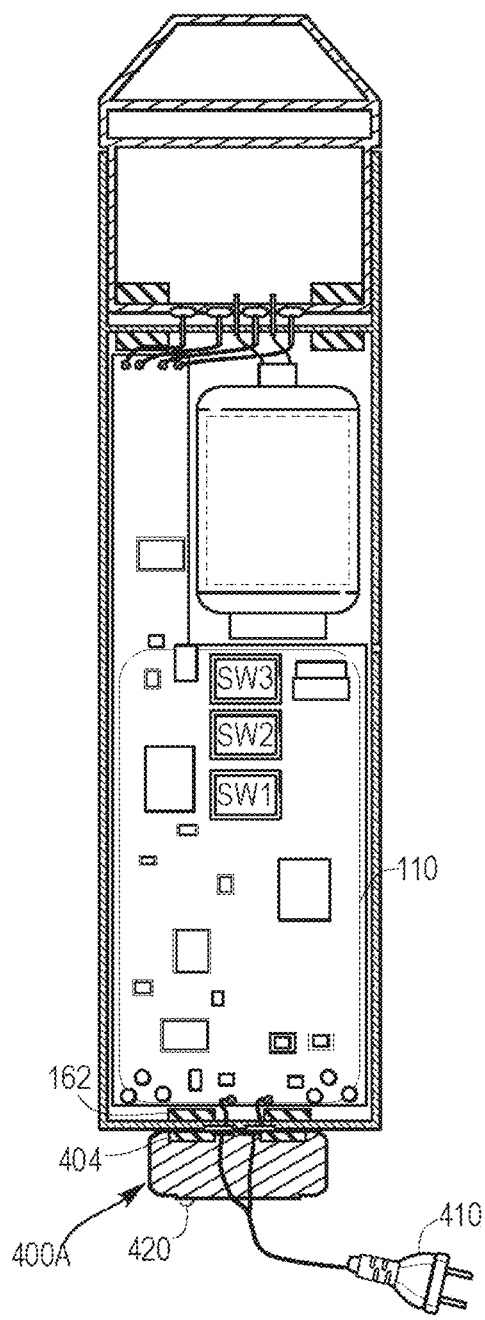

VAPORIZER

CROSS REFERENCE TO RELATED APPLICATIONS

This application claims the benefit of U.S. Provisional Application Nos. 61/903,344 filed Nov. 12, 2013, 61/937,851, filed Feb. 10, 2014, U.S. Provisional Application No. 62/015,148, filed Jun. 20, 2014, and U.S. patent application Ser. No. 14/539,801 filed Nov. 12, 2014, the disclosure of which are hereby incorporated herein by reference in their entireties.

FIELD OF THE INVENTION

This invention relates to the field of vaporizers, which may also be referred to as electronic cigarettes.

BACKGROUND

Electronic cigarettes have recently emerged as a new product for providing nicotine through a smokeless inhalation process. Typically, implementations consist of a power supply (typically a battery) and an atomizing device. In reusable electronic cigarettes the two items are separated into a battery and a cartomizer, to allow the disposal and replacement of a nicotine containing fluid cartomizer while preserving the more costly battery and associated circuitry (microcontroller, switch, indicating LED, etc.) for additional use. In disposable electronic cigarettes, the two items are combined to integrate the functions into one unit that is discarded after either the battery energy or the nicotine containing liquid is exhausted.

The electronic cigarette liquid used to vaporize ingredients such as nicotine is generally a solution of propylene glycol (PG), vegetable glycerin (VG), or polyethylene glycol 400 (PEG400), as well as their mixtures to which a flavor and/or nicotine has been added. The solution is often sold in a bottle (for refilling by the user) or in disposable cartridges or cartomizers. Many different flavors are incorporated into these liquids, including those that resemble the taste of regular tobacco, menthol, vanilla, coffee, cola and/or various fruits. Various nicotine concentrations are also available, and nicotine-free solutions are also common.

BRIEF SUMMARY

Embodiments of a vaporizer, in accordance with the disclosure, may include a shell having a battery segment and a cartomizer receiving segment, the cartomizer receiving segment defining a chamber having an insertion end distal from the battery segment and a base end proximate to the battery segment; a cartomizer insertable into the chamber at the insertion end, the cartomizer including: an outer cartomizer shell, a holding structure provided within, and secured to, the outer cartomizer shell, the holding structure including a basin dimensioned to hold a vaporizable substance, a heating element provided within the basin operable to heat the vaporizable substance, cartomizer electrical contacts provided on the exterior of the cartomizer, cartomizer electrical circuitry operable to direct an electronic current between the cartomizer electrical contacts and the heating element, and a mouthpiece fluidly communicable with the basin, the mouthpiece extending from the insertion end of the chamber when the cartomizer is inserted in the chamber, wherein the heating element is activated by the current and is operable to heat the vaporizable substance to a vaporization temperature; a battery housed within the battery segment; battery electrical contacts provided between the base end of the chamber and the battery segment, the battery electrical contacts positioned to contact the cartomizer electrical contacts when the cartomizer is inserted in the chamber; battery electrical circuitry housed within the battery segment and operable to direct an electrical current between the battery, the battery electrical contacts, the cartomizer electrical contacts, the heating element, and the inserted cartomizer.

BRIEF DESCRIPTION OF THE FIGURES

FIG. 1 illustrates a front view of an embodiment of an electronic cigarette of the disclosure comprising a first embodiment of a battery portion with an embodiment of a cartomizer for use with a vaporizable liquid inserted into a cartomizer chamber of the first embodiment battery portion, the outer shell of the first embodiment battery portion shown transparently so as to illustrate the inner components of the electronic cigarette.

FIG. 1A illustrates a lateral cross sectional view of the electronic cigarette of FIG. 1 illustrating an electrical connector and magnets.

FIG. 1B illustrates a lateral cross sectional view of the electronic cigarette of FIG. 1 illustrating the end of the inserted cartomizer.

FIG. 1C illustrates a lateral cross sectional view of the electronic cigarette of FIG. 1 illustrating the cartomizer chamber.

FIG. 2 illustrates a front view of an embodiment of a cartomizer in accordance with the disclosure that may be inserted into the cartomizer chamber of the battery portion of FIG. 1, the outer shell of the first embodiment battery portion shown transparently so as to illustrate the inner components of the electronic cigarette.

FIG. 2A illustrates a lateral cross sectional view of the cartomizer of FIG. 2 illustrating the end of the cartomizer at the inserted end.

FIG. 2B illustrates a lateral cross sectional view of the cartomizer of FIG. 2 illustrating the air hole structure.

FIG. 13 illustrates a front view of an embodiment of an electronic cigarette in accordance with the disclosure, with the outer shell of the embodiment of the battery portion shown transparently so as to illustrate the inner components of the electronic cigarette.

FIG. 14 illustrates a front view of the electronic cigarette of FIG. 13 with a charger attached.

DETAILED DESCRIPTION

Figure 2C:
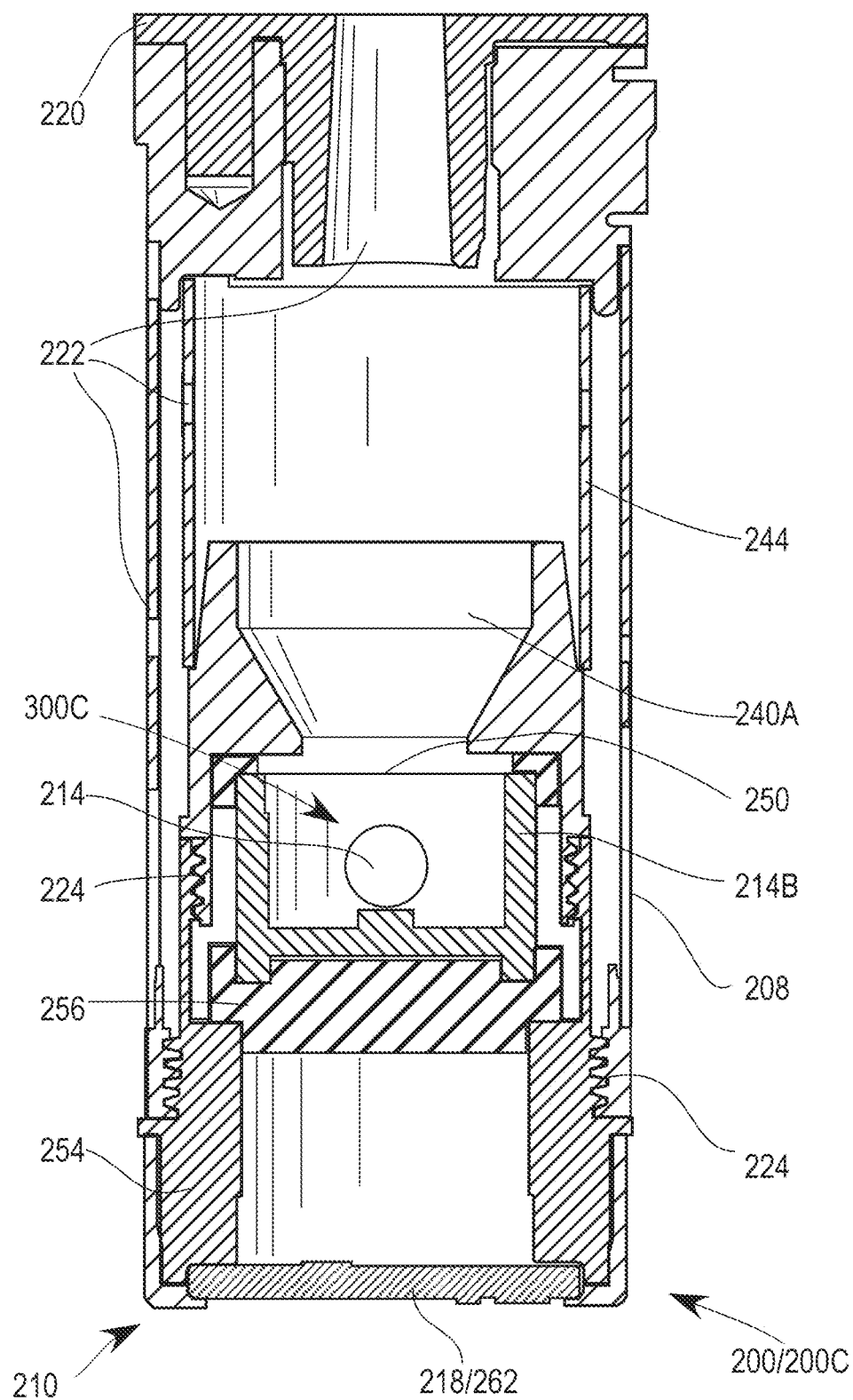
FIG. 2C illustrates a front view of an embodiment of a cartomizer in accordance with the disclosure that may be inserted into the cartomizer chamber of an embodiment of a battery portion of the disclosure, the outer shell of the first embodiment battery portion shown transparently so as to illustrate the inner components of the electronic cigarette.

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings are not to scale and in certain instances details have been omitted, which are not necessary for an understanding of the present invention, such as conventional details of fabrication and assembly.

Embodiments of a vaporizer, in accordance with the disclosure, may include a shell having a battery segment and a cartomizer receiving segment, the cartomizer receiving segment defining a chamber having an insertion end 108A distal from the battery segment and a base end 108B proximate to the battery segment; a cartomizer insertable into the chamber at the insertion end, the cartomizer including: an outer cartomizer shell, a holding structure provided within, and secured to, the outer cartomizer shell, the holding structure including a basin dimensioned to hold a vaporizable substance, a heating element provided within the basin operable to heat the vaporizable substance, cartomizer electrical contacts provided on the exterior of the cartomizer, cartomizer electrical circuitry operable to direct an electronic current between the cartomizer electrical contacts and the heating element, and a mouthpiece fluidly communicable with the basin, the mouthpiece extending from the insertion end of the chamber when the cartomizer is inserted in the chamber, wherein the heating element is activated by the current and is operable to heat the vaporizable substance to a vaporization temperature; a battery housed within the battery segment; battery electrical contacts provided between the base end of the chamber and the battery segment, the battery electrical contacts positioned to contact the cartomizer electrical contacts when the cartomizer is inserted in the chamber; battery electrical circuitry housed within the battery segment and operable to direct an electrical current between the battery, the battery electrical contacts, the cartomizer electrical contacts, the heating element, and the inserted cartomizer.

Further embodiments of a vaporizer may include a container having container walls provided proximate to the basin, the container dimensioned such that the vaporizable substance may pass from the container to the basin. The holding structure may further includes a stabilizing element connectable with the outer cartomizer shell, the basin secured to the stabilizing element. The stabilizing element may includes a first threaded portion threadably connectable with the outer cartomizer shell. The vaporizer may also include a container including container walls and a threaded container portion, the container dimensioned such that the vaporizable substance is passable from the between the container walls to the basin, and the stabilizing element includes a second threaded portion threadably engagable with the threaded container portion. The vaporizer may include at least one air passage provided through at least one hole in the outer shell and at least one hole in the container wall. The vaporizable substance may be a wax. The vaporizer may further include a cartomizer printed circuit board in electronic communication with the cartomizer electrical circuitry.

With reference now to FIGS. 1 and 2, an embodiment of an electronic cigarette 10 is provided in accordance with the disclosure. Electronic cigarette 10 may include a battery portion connectable with a vaporization unit or cartomizer 200 for holding a vaporizable substance 300. The battery portion may include a battery housing segment 102 provided proximate to the first end 102A of the battery portion, and a second cartomizer receiving segment 104 provided proximate a second end 104A of the battery portion. The battery portion may include an outer shell 106 for covering or protecting one or more of the components of battery portion 100 as may be internally provided as described herein. Outer shell 106 may be substantially constructed from metal, plastic, or any other known or to be developed material suitable for protecting internal components of electronic cigarette 10, including the electrical components described herein. Battery housing segment 102 and cartomizer receiving segment 104 may commonly share outer shell 106. A cartomizer chamber 108 may be provided within at least a portion of cartomizer receiving segment 104. A cartomizer 200 may be insertable into the cartomizer chamber 108 in accordance with embodiments of the disclosure. Shell 106 may cover cartomizer chamber 108 thereby protecting an inserted or received cartomizer 200.

Electrical components for operating electronic cigarette 10 may be provided within battery housing segment 102. A battery 110 may be provided in order to provide electrical power as may be required by various features of the electronic cigarette 10. In some embodiments, battery 110 may be disposable, such as an AA or AAA cell battery, while in other embodiments, battery 110 may be of a rechargeable type, for example a 13450 lithium ion battery, an 18650 2600 mAh lithium ion cell, or flat lithium ion 903180 cell rated at 2300 mAh. Multiple batteries 110 may be used in series to generate higher voltages capable of shortening times to achieve vaporization temperatures in the cartomizer 200. A printed circuit board (PCB) 112 may also be provided for controlling one or more functions of electronic cigarette 10. PCB 112 may be electrically connected to battery 110 through circuitry in order to direct current flow as required in accordance with the disclosure. PCB 112 may include one or more integrated circuit chips as well as a micro control unit. A boost chip may also be provided in order to amplify voltage with at least portion of circuitry, as may be required in order to accomplish various functions described herein. PCB 112 may include a light emitting diode (LED), a microcontroller, a plurality of capacitors, a plurality of transistors, and a plurality of resistors or any combination thereof. An accelerometer for sensing gravity shifts of electronic cigarette 10 may be further provided. The accelerometer may be operable to detect tilting or changes in orientation of battery portion 100, and PCB 112 may be accordingly operable to react to a shift in orientation detected by the accelerometer. For instance, electronic cigarette 10 including an accelerometer may be activated by shaking or inverting electronic cigarette 10. Any known or to be discovered circuitry or arrangement of the components of PCB 112 are contemplated within the disclosure in order to achieve the desired functions of electronic cigarette 10 as described herein.

A variety of indicator lights forming one or more illuminative indicators may be provided in embodiments of the disclosure. One such indicator may be a battery end indicator 114 provided as a ring extending about at least a portion of shell 106 at or proximate to first end 102A. In one such embodiment, battery end indicator 114 may be provided at or proximate to first end 102A and includes one or more LED lights having one or more colors. Each color may, for instance, indicate a status of electronic cigarette 10. The status may be associated with the power remaining of battery 110, an activation state of electronic cigarette 10, the heating level of an inserted cartomizer 200, or any other status which may be desirable to communicate to a user of electronic cigarette 10 through a light color. For instance, when electronic cigarette 10 is activated such that a user is either actively inhaling cigarette 10, as described in accordance with disclosure, or cigarette 10 is in a state such that the user could inhale, indicator 114 may be red or reddish. In such an embodiment, battery end indicator 114 could extend about at least a portion of the first end 102A such that when indicator 114 emanates a red or reddish color a user may associate the red color at or proximate to first end 102A with the red glow of a lit cigarette. In another embodiment, an indicator ring may be provided to illuminate one or more colors associated with the charge or power state of battery 110. For instance, battery end indicator 114 may illuminate green or blue when the battery is operating with a sufficient charge, and yellow or red when the battery is operating with a low charge such that the user should consider charging battery 110, in accordance with the disclosure. A ring indicator 116 may be provided on or proximate to an activation button 118, which may function to activate cigarette 10 as described herein in accordance with the disclosure. While activation button 118 may be provided on the surface of outer shell 106, and ring indicator 116 may substantially circumference button 118. Ring indicator 116 may include one or more LED lights having one or more colors to indicate various statuses of electronic cigarette 10. Status changes of electronic cigarette 10, such as insertion of cartomizer 200, activation of electronic cigarette 10 by pressing button 118, or deactivation of electronic cigarette 10 by pressing button 118 an additional time may each result in a different associated and predetermined color. The activation of the appropriate LED light or lights may be controlled by PCB 112. In embodiments where button 118 is coplanar or aligned with the surface of outer shell 106, as described herein, ring indicator 116 may also be coplanar or aligned with button 118 and the surface of outer shell 106. Another indicator light may be provided at or proximate to cartomizer end 104A. In one embodiment, in order to transmit a lighting effect from the battery segment 102, where battery 110 and PCB 112 may be housed, to the cartomizer end 104A, one or more LED lights may be provided in the cartomizer receiving segment 104 at or proximate to the battery segment 102. One or more clear tubes or optic fibers may be also be provided within or just below the surface of outer shell 106, with the tubes or fibers terminating at or proximate to the cartomizer end 104A. The resulting effect is an attractive, illuminative effect where the LED lights provided in the cartomizer segment are projected into and transmitted along the fibers. PCB 112 could potentially alternate or change the LED light colors projected into the fibers. The color alternation could be periodic, creating a steady change of colors, or the color alteration could be responsive to a status change of the electronic cigarette 10.

In order to provide an electrical connection between PCB 112 and an inserted cartomizer 200, an electrical connector 120 may be provided and may include a plurality of pogo pins 120. Pogo pins are devices used to establish connections between two circuits, and each may take the form of a cylinder containing one or more spring-loaded pins 122, each retractable upon compression, for instance by cartomizer 200 when it is inserted in cartomizer chamber 108. In one such embodiment, three pogo pins 122 may be provided, one for establishing positive current connection, one for establishing a negative current connection, and one for establishing a ground current connection. Each pogo pin 122 may be connected to PCB 112, which may control current outputted to pogo pins 122. For instance, PCB 112 may operate to vary or intermittently activate current flow to connector 120, the variation thereby regulating the activation of a heating element in a connected cartomizer. When cartomizer 200 is not received in cartomizer chamber 108, a head portion of each pogo pin may extend into cartomizer chamber 108. When cartomizer 200 is received in cartomizer chamber 108, the pins 122 are contacted and at least partially compressed into battery portion 102. Pins 122 may be contacted or pressed against electrical receivers provided on cartomizer 200 as described herein, thereby establishing an electrical connection between PCB 112 and cartomizer 200. Additional pins 122 are contemplated in embodiments of the disclosure, such as a fourth pin for providing an electrical connection to another element, such as the LED lights described above or a temperature sensor 260 described herein and illustrated in FIG. 2.

An additional embodiment of connector 120 may operate to identify information from an inserted cartomizer 200 based on voltage drop over one or more pins 122. For instance, connector 120 may include a controlling pin 122 from which connected PCB 112 may detect variations in voltage drop across the pin when connected to various types of cartomizers 200. Circuitry provided within a first type of cartomizer 200 may effectuate a first voltage drop over a controlling pin 122, while circuitry provided within a second type of cartomizer 200 may effectuate a second voltage drop over controlling pin 122 when cartomizer 200 is inserted in chamber 108. If PCB 112 detects a first voltage drop, the cartomizer 200 is identified as a first type of cartomizer, whereas if PCB 112 detects a second voltage drop, the cartomizer is identified as second type of cartomizer. A first cartomizer type may hold a first type of vaporizable substance 300, while a second cartomizer type may hold a second type of vaporizable substance 300. In one embodiment, connector 120 includes three pins 122: a positive pin, a ground pin, and a controlling pin. A controlling pin may also serve a dual function in that communication between a sensor 260 may also occur through a controlling pin 122. Other known or to be developed devices or connectors are contemplated within the disclosure for establishing an electrical current between PCB 112 and cartomizer 200.

Various features may be further provided in embodiments of electronic cigarette 10 in order to secure and align cartomizer 200 within cartomizer chamber 108. For instance, at least one magnet 124 may be provided in or proximate to chamber 108. A magnet 202 of opposing polarity to magnet 124 may be placed on a surface of cartomizer 200 so as to secure cartomizer 200 within chamber 108 when magnets 124, 202 (see FIGS. 1A, 1B) contact each other. It should be understand and appreciated that, in some embodiments, battery portion magnet(s) 124 may attach to cartomizer metallic surface(s) 202 and, conversely, cartomizer magnet(s) 202 may attach to battery portion metallic surface(s) 124, thereby establishing a magnetic connection between battery portion 100 and cartomizer 200. Other known or to be discovered means of securing cartomizer 200 in cartomizer chamber 108 are contemplated within the disclosure, including but not limited to, snap fit connectors, friction fit, threaded insertion of cartomizer 200 into chamber 108, a suction fit using pressurized means or any other suitable method of securing known or to be developed in the art.

One or more alignment features or mechanism may be included in order to ensure proper placement of cartomizer 200 in cartomizer chamber 108. In one embodiment, two magnets 124 may be provided proximate to connector 120 (see FIG. 1A), each magnet 124 having an opposed polarity. In this embodiment, two cartomizer magnets 202 (see FIG. 1B) may be provided of opposing polarity at an insertion end 210 of cartomizer 200. Because of the opposing polarities of magnets 124/202, the cartomizer 200 may only be inserted and secured in one direction or orientation, thereby facilitating alignment of cartomizer 200 within chamber 108. An alignment protrusion or peg 126 (see FIG. 1C) may be provided on a portion of an interior surface of chamber 108, and an alignment slit or slot 204 may be provided on a portion of cartomizer 200. Alignment protrusion 126 may be dimensioned to fit or slid along slit 204 so that cartomizer 200 may only be inserted in a particular, proper orientation. In another embodiment, a slit, crevice, or cutout may be provided on a portion of shell 106, with a matching protrusion provided on a portion cartomizer 200. For instance, a cutout may be provided on an upper rim of shell 106 at cartomizer receiving segment 104, while a matching protrusion may be provided on a portion of cartomizer 200 proximate to insertion end 210, with battery portion cutout engageable with the cartomizer protrusion when the cartomizer is properly aligned so as to ensure proper orientation of cartomizer 200 within chamber 108. Ensuring cartomizer 200 is properly oriented within chamber 108 in turn ensures proper contacting of cartomizer 200 with connector 120, and therefore proper functioning of electronic cigarette 10.

One or more windows 130 may be provided in outer shell 106 (see FIG. 1). Windows 130 may be made of a translucent material, such as glass or substantially clear plastic, in order to view internal components of battery portion 100. Window 130 may also be a slit cut into shell 106. For instance, in one embodiment, window 130 may be provided on or proximate to cartomizer receiving segment 104 and, more particularly, cartomizer chamber 108 so as to permit a user of electronic cigarette 10 to view the cartomizer 200 when it is inserted into cartomizer chamber 108.

One embodiment of cartomizer 200 for holding vaporizable material 300 is cartomizer 200A for holding a vaporizable fluid 300A, an embodiment of which is illustrated in FIG. 1. Vaporizable fluid 300A may be, for example, any known or to be developed fluid useful to vaporize, for inhalation nicotine, flavor or other desired ingredients in an electronic cigarette, such fluids include propylene glycol (PG), vegetable glycerin (VG), or polyethylene glycol 400 (PEG400), as well as their mixtures to which a flavor and/or nicotine has been added. Cartomizer 200A may be substantially elongate and insertable into chamber 108. Chamber 108 is defined by outer shell 106 and electrical connector 120. An insertion end 210 of cartomizer 200A, defined opposite of a mouthpiece end 212, may be inserted into the chamber first and may ultimately contact or be positioned proximate to connector 120 of battery portion 100. Cartomizer 200A may include a body 208 for holding fluid 300A. At least a portion of body 208 may be composed of translucent or substantially translucent material, such as glass or plastic, so that a user may see fluid 300A held within. The portion of body 208 composed of translucent material may be alignable with window 130 and may be proximate to LED lights or fiber optics so as to illuminate cartomizer 200A as it is inserted into chamber 108. The illumination may occur automatically upon insertion, or may be programmed to illuminate upon activation or manipulation of a switch, such as button 118.

In order to vaporize fluid 300A, a heating element 214 and a wicking element 216 may be provided within cartomizer body 208. An electrical current may be transmitted to heating element 214 through circuitry in electrical communication with electrical contacts, which contact pins 122 (see FIG. 1A) when cartomizer 200A is inserted into chamber 108. Once fluid 300A is heated to an optimal vaporizing temperature, the user may inhale the vaporized fluid 300A through a mouthpiece 220 provided on body 208 at or proximate to mouthpiece end 212. The vaporized fluid may travel through an inhalation tube 222 in fluid connection with heating element 214 and wick 216. Inhalation tube 222 may also be in fluid communication with one or more holes or ducts provided, for instance, in sides of outer shell 106 in order to permit air flow through cartomizer body 208. The electrical current transmitted to heating element 214 may be controlled by PCB 112 through connector 120 when cartomizer 200A is inserted into chamber 108. The electronic cigarette 10 may be manually controlled, as a user may press button 118 to initiate a charge to heating element 214, which in turn may heat fluid 300A to a vaporized temperature which a user may inhale through mouthpiece 220. An automatically heating version of electronic cigarette 10 is also contemplated with disclosure, where a pressure switch integrated with connector 120 may activate current flow from PCB to heating element 214 rather than by manual activation from switch 118.

So that a user may refill fluid 300A held in body 208, mouthpiece 220 may be removable from body 208. Mouthpiece 220 may include a screw thread 224 so that mouthpiece 220 may be threadably engaged with mouthpiece end 212 of body 208 or, alternatively, may be press fit onto or into mouthpiece end 212 of body 208. A bushing 226, which may be a ring formed from plastic, rubber, or any other suitable material, may be provided to help stabilize and retain cartomizer 200 tightly fit in chamber 108. Additionally, a colored ring or logo 228 may be provided about a portion of cartomizer body 208 in order to identify the type or cartomizer being used.

With reference now to FIGS. 2, 2A and 2B, an additional embodiment of cartomizer 200B is provided for holding a dry vaporizable material 300B, such as dry tobacco. A container 240 may be provided within cartomizer body 208. Container 240 may be made from a material having a high thermal conductivity, such as metal, in order to transmit heat from a heating element 214A provided about at least a portion of container 240. In that at least a portion of heating element 214A may be provided about at least a portion of container 240, the material 300B provided within container 240 may be heated from multiple sides, similar to an oven, as opposed to from a single concentrated heat source. As an electrical current is transmitted to heating element 214A, the interior of container 240 may be heated to a desired vaporizing temperature. Heating element 214A may be substantially comprised of a non-conductive material, such as a polyimide flex harness material, with a conductive material, such a copper or other metal wiring shaped into a wire or flat ribbon, dispersed throughout the non-conductive material. The conductive material may be intertwined or wound throughout the non-conductive material in order to increase the heated surface area as well as to increase the impedance of the conductive material, which may then be electrically connected to PCB 112 through connector 120 when cartomizer 200B (See FIG. 2) is inserted in cartomizer chamber 108 (See FIG. 1). The impedance value of the conductive material may be 2-3 ohms in some embodiments, and in other embodiments a maximum of 1 ohm. In some embodiments, heating element 214A may be provided around the majority of cartomizer body 208, and in some embodiments heating element 214A may be provided proximate to only a portion of cartomizer body 208. For instance, heating element 214A may be provided only proximate to insertion end 210, in order to provide a greater portion of heating through convection rather than through conduction. In some embodiment, heating element 214A may be provided about all or the majority of body 208, and PCB 112 may be operable in order to vary the amount of heating provided through convection rather than conduction. For instance, only the portion of heating element 214A proximate to insertion end 210 may be activated in order to heat vaporizable substance 300B through convection, or all or nearly all portions of heating element 214A may be activated in order to increase the conduction heating of substance 300B. PCB 112 may operate to switch between a conduction heating and a convection heating.

An insulating material 242 may be further provided within body 208 in order to control or regulate the heat distribution. Insulating material 242 may be provided around at least a portion of the exterior of heating element 214A in order to insulate body 208 from excess heat temperature, which may transmit to outer shell 106 (See FIG. 1). Insulating material 242 may also be provided between heating element 214A and container 240 so as to regulate or control heat transmitted to container 240.

One or more screens 250 may be provided within body 208 in order to contain dry material 300B within container 240, as well as to filter circulated air. Air may be circulated by providing one or more holes 252 in the cartomizer body 208. In one embodiment, holes 252 form a "t" shape (See FIG. 2B) from which the center of the "t" is substantially aligned with a hole leading to container 240. Holes 252 may be capable of alignment with one or more holes on the outer shell 106 of battery portion 100 so that air from the environment may pass through holes 252 and into container 240 where material 300B is provided. Holes 252 may be provided proximate to the inserted end 210. Screens 250 may be provided either at or proximate to inserted end 210, mouthpiece end 212, or both. In some embodiments, container 240 is removable from the rest of cartomizer body 208. Mouthpiece 220 may be removable or detachable, for instance through a screw thread, so as to permit access to container 240. An upper screen 250 may be attached or manufactured integrally with mouthpiece 220 so as to be removed with mouthpiece 220.

A sensor 260 may be included in some embodiments of cartomizer 200. Sensor 260 may operate to sense vaporizing temperature, and may be electronically communicative with PCB 112 so as to provide sensory information to PCB 112, which may be consequently transmitted to one of the LED indicators provided in electronic cigarette 10 as described in accordance with the disclosure. For instance, indicator 118 (See FIG. 1) may illuminate a certain color when sensor 260 has detected that vaporization temperature in container 240 has been reached and the user may proceed to inhale vaporized material 300. PCB 112 may also including safety protocols for automatic shutoff in the event that sensor 260 records a temperature above a preset vaporization temperature range, which may indicate material 300 (including, for example, 300A, 300B, 300C) is actively burning or about to burn. Thus, sensor 260 may operate as a thermistor. A vaporization range for many materials 300 may be between about 190 degrees Celsius and about 240 degrees Celsius, and in some embodiments the vaporization temperature may be at about 230 degrees Celsius. In this vaporization temperature range, active ingredients of the vaporization material 300 may begin to vaporize without actively burning, which may occur at about 400 degrees Celsius or higher for some materials. PCB 112 may operate to control the vaporization temperature, for instance regulating a maximum vaporization temperature or controlling the vaporization actual temperature. In one embodiment, PCB 112 may control or regulate vaporization temperature within 10 degree Celsius, and in another embodiment PCB 112 may more finely control or regulate vaporization temperature within 1 degree Celsius, based on a selected or desired vaporization temperature as inputted by a user of electronic cigarette 10. It should be understood and appreciated that communication between sensor 260 and PCB 112 may be bidirectional so that sensor 260 may operate to control at least portions of vaporizer functions or to transmit information to PCB 112 and additionally receive information from PCB 112, which operates to control electronic cigarette 10.

FIG. 2C illustrates an additional embodiment of cartomizer 200C which may be inserted into cartomizer chamber 108 (FIG. 1) and utilized for vaporization of a vaporizable wax 300C. Cartomizer 200C may include an outer cartomizer shell or body 208 for housing and protecting internal components of cartomizer 200C. Outer shell 208 may include a threadable end 224 provide proximate to insertion end 210, and distal to mouthpiece 220. In one embodiment, mouthpiece 220 may be connected to outer shell 208 while in another embodiment mouthpiece 220 may be removable from outer shell 208, for instance from threading or a friction held push fit. Through threading 224 proximate to insertion end 210, outer shell 208 may be threadably engagable with a holding structure 254, which may be provided for securing a heating element 214 provided within a bowel or basin 214B. As part of holding structure 254, a stabilizing element may be provided 256. In one embodiment, basin 214B is secured to stabilizing element 256. Stabilizing element 256 may be constructed for silicone rubber or any other known or to be discovered material which may be provided to secure basin 214B while embodying the necessary thermal properties for contacting basin 214B. In one embodiment, basin 214B is composed of ceramic. Proximate to basin 214B may be a wax container 240A, and a screen or mesh 250 may be provided between basin 214B and container 240A. Container 240A may include a threaded portion 224 for removable engaging with holding structure 254. In this regard, holding structure 254 may feature two threadings 224—a first threading for engagement with outer shell 208 and a second threading for engagement with container 240A. A container cover 244 may be further provided and may include cover walls which substantially surround the upper and open portion of container 240 opposite heating element 214 and basin 214B. In one embodiment, cover 244 is secured to a portion of mouthpiece 220 such that when outer cover 208 is removed along with mouthpiece 220, cover 244 is further removed thereby exposing container 240A so that it may be refilled with additional wax 300C. Airflow passage 222 may be provided as a first passage within the wall of container cover 244, a second passage within the wall of outer shell 208, and an tube leading through mouthpiece 220. Multiple first passages and multiple second passages may be provided as described. In order to discourage back flow of vapor, the one or more first passages may be placed closer to mouthpiece 220 than the one or more second passages. In this arrangement, vaporized wax 300C may travel from heating element 214 through container 240A and the first passage within the wall of cover 244, through a circumferentially outer passage between cover 244 and outer shell 208, and out through mouthpiece 220 as a user inhales. Electrical wiring may be provided from heating element 214 to a cartomizer PCB 262, which may operate to control the functioning of the cartomizer including activation of heater 214. In association with PCB 262 may be electrical contacts 218 for permitting electrical communication with battery portion 100.

Figure 3:
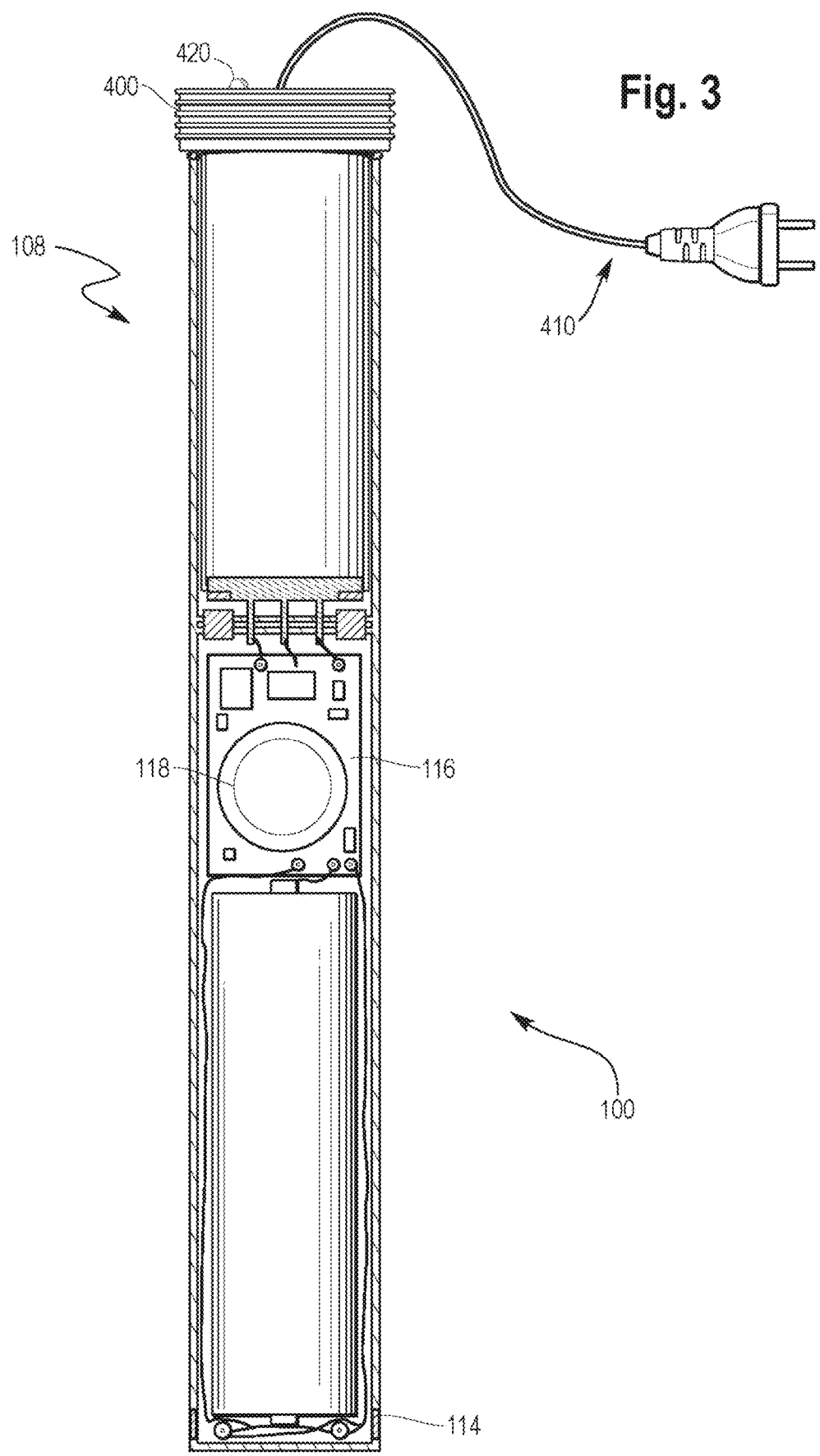
FIG. 3 illustrates a front view of an embodiment of the battery portion of FIG. 1 with an embodiment of a charger, in accordance with the disclosure, inserted into the cartomizer chamber, with the outer shell of the first embodiment battery portion shown transparently so as to illustrate the inner components of the electronic cigarette.
Figure 4:
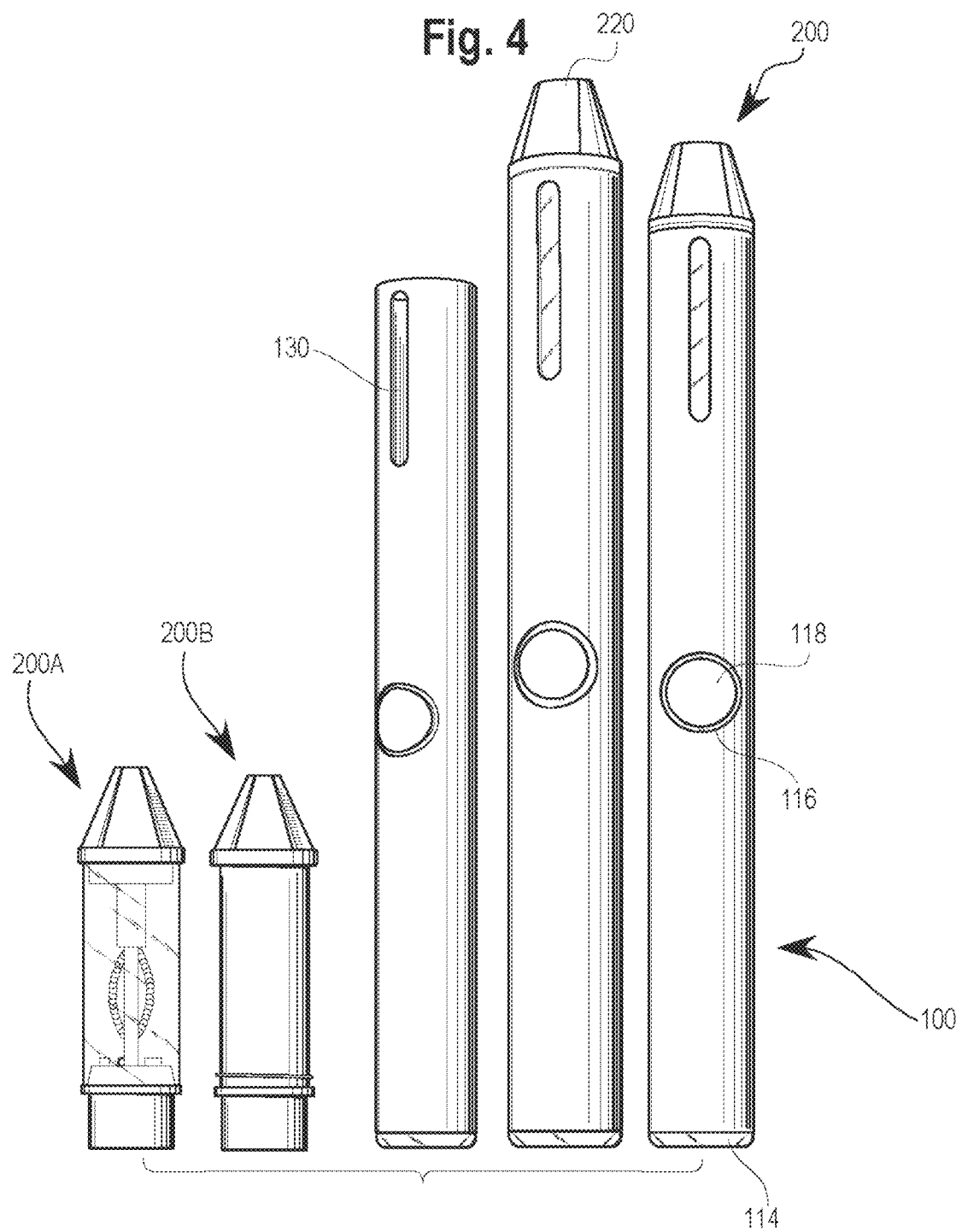
FIGS. 4-7 illustrate embodiments of electronic cigarettes comprising the first battery portion of FIGS. 1-3 and the cartomizers of FIGS. 1 and 2, in accordance with the disclosure.
Figure 5:
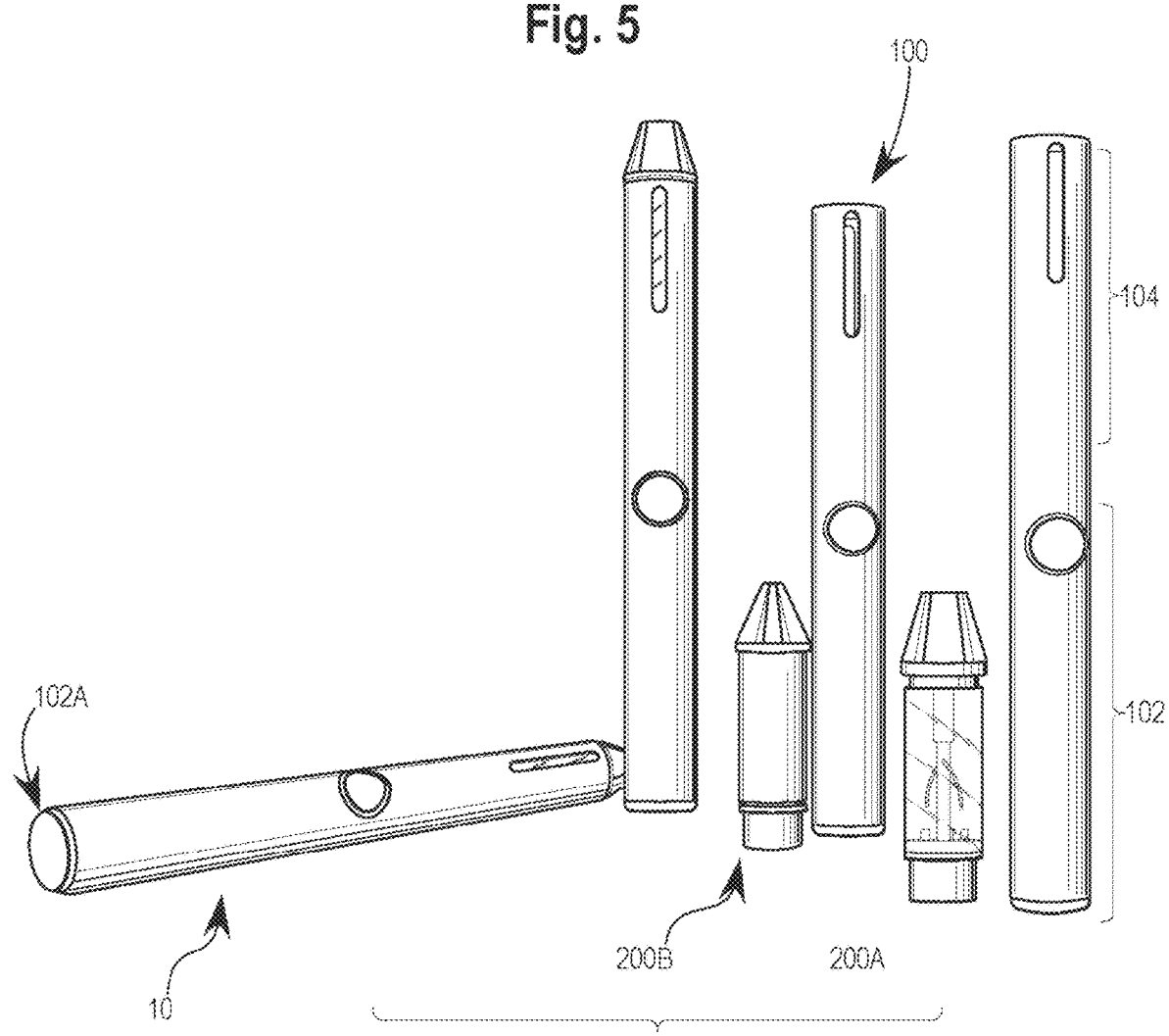
Figure 6:
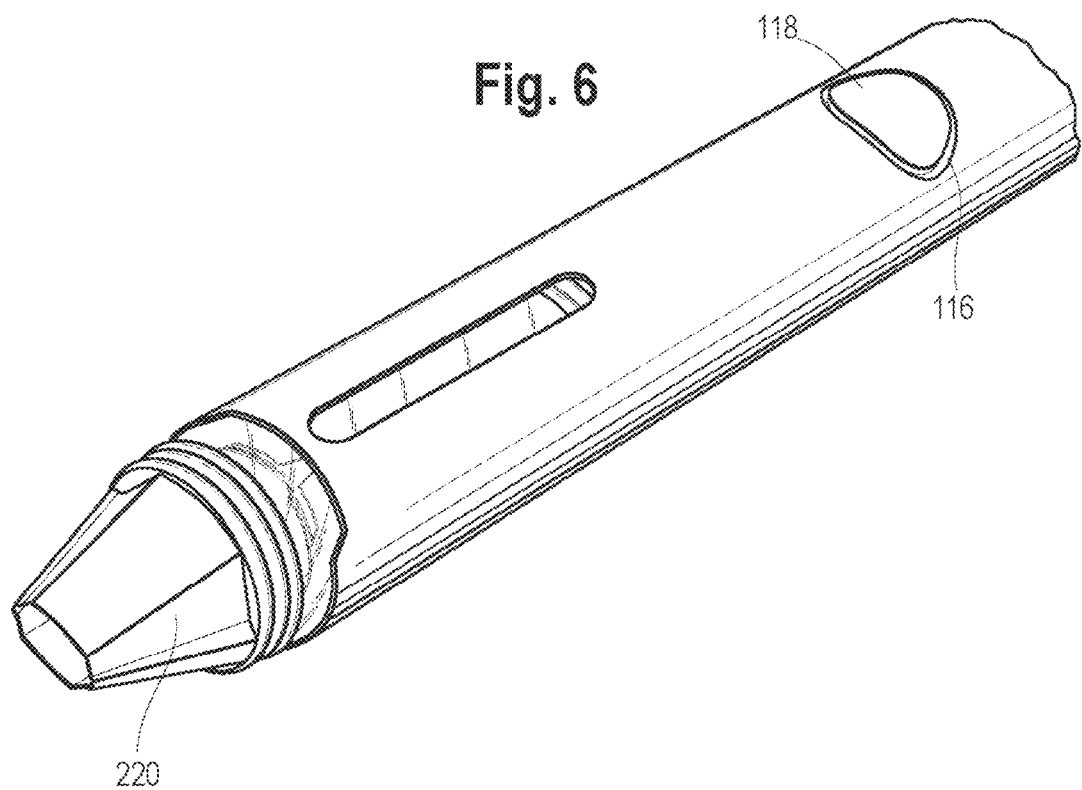
Figure 7:
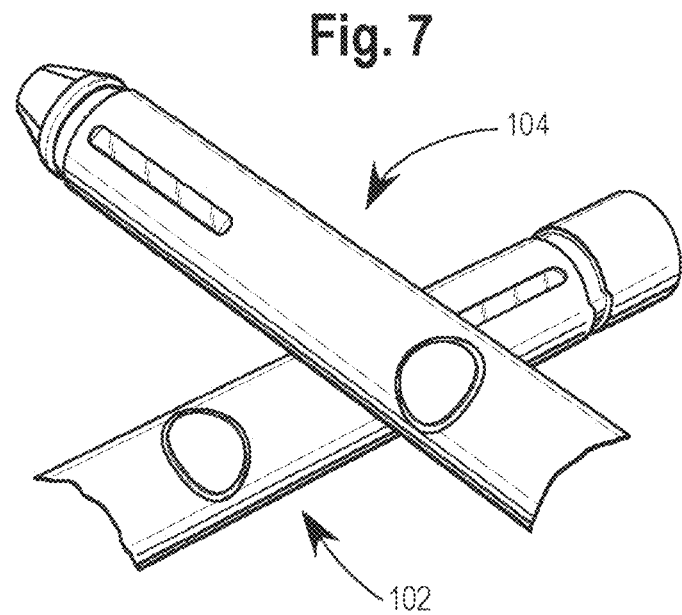

As shown in FIG. 3, a charger 400 may be inserted into chamber 108 (FIG. 1) in order to charge battery 110 (FIG. 1) in embodiments where battery 110 may be rechargeable. Through its insertion into chamber 108 and contact with connector 120, charger 400 may provide an electrical charge to battery 110. Charger 400 may include a plug 410 for connecting charger 400 to a power source, which in one embodiment is a wall socket. Other plugs 410 for different power sources are contemplated within the disclosure, including USB connections and other known or to be developed power sources. An indicator light 420, which may be an LED light, may be provided on charger 400 in order to indicate a charging status, for instance when charger 400 is connected with a power source. PCB 112 may operate to change other indicators, for instance LED indicators 114/116, to indicate the charging status of electronic cigarette 10. In accordance with the disclosure, and illustrated for instance in FIG. 9, charger 400 may be connectable to battery portion at or proximate to first end 102A. Furthermore, as also illustrated for instance in FIG. 9, charger magnets 404 are contemplated within the disclosure in order to securely couple charger 400 to battery portion 100. In one embodiment, a metallic surface 404 is provided and positioned so as to be adjacent to magnets 124 or magnets 162 (depending on the embodiment of the disclosure). In another embodiment, a metallic surface 124 or 162 in order to magnetically couple battery portion 100 with charger magnets 404. Additionally, charger magnets 404 may be provided having opposing polarities as battery portion magnets 124 or 162.

With regards to PCB 112, as previously discussed for instance in reference to FIG. 1, and related electrical components, functioning, and control of vaporizer 100, a variety of controls or commands are contemplated in associated with the operation of vaporizer 100. Various LED indicators 114, 116 may be utilized in conjunction with PCB 110 in showing operation states or statuses of vaporizer 100. For instance, the pressing of button 118 a preset number of times, which may be 3 times, within a preset time period, which may be 2 seconds, may result in locking or unlocking the vaporizer. Ring indicator 116 may then change illuminated colors to indicate a lock state of vaporizer 100. In a lock state, vaporizer may not function to activate a heating element 214/214A/214B of an inserted cartomizer 200. A low battery voltage may also be indicated to a user by illuminating and possibly flashing a predetermined color through indicator 116. In one embodiment, a low battery state is indicated when the battery voltage of battery 110 falls below about 3.2V. Activation of heating element 214/214A/214B may be accomplished by pressing or holding button 118. A cutoff feature may programmed into either PCB 112 or cartomizer PCB 262 such that heating element 118 will be disabled if button 118 is actuated for longer than a preset time, which may be 10 seconds in one embodiment and 30 seconds in another embodiment. While button 118 is actuated, and accordingly heating element 214 of an inserted cartomizer 200 is activated, indicator 116 may illuminate a predetermined color. Additionally, PCB 112 may operate to detect the type of inserted cartomizer 200, namely what type of vaporizable substance 300 the inserted cartomizer 200 is designed to hold and vaporize, and accordingly ring indicator 116 may illuminate a preset color associated with the inserted cartomizer 200 type. For instance, ring indicator may illuminate in a white, red, and green color when a first, second, and third cartomizer type is inserted, respectively. For some vaporizable substances 300, particularly many varieties of dry tobacco 300B, heating element may need to heat the substance for a certain time period before the substance is vaporized and may be inhaled by the user. In this situation, button 118 may be held for a certain time, which may be 3 seconds, before ring indicator illuminates indicating the user may inhale the vaporized substance. Furthermore, in the event an error in the PCB 112 programming occurs, a reset feature may be incorporated. For instance, pressing and holding button 118 for a certain time period, which may be three (3) seconds, while no cartomizer is inserted may operate to reset the programming to a default programming.

FIGS. 4-7 further illustrate the embodiments of electronic cigarette 10 provided in FIGS. 1-3, in accordance with the disclosure.

Figure 8:
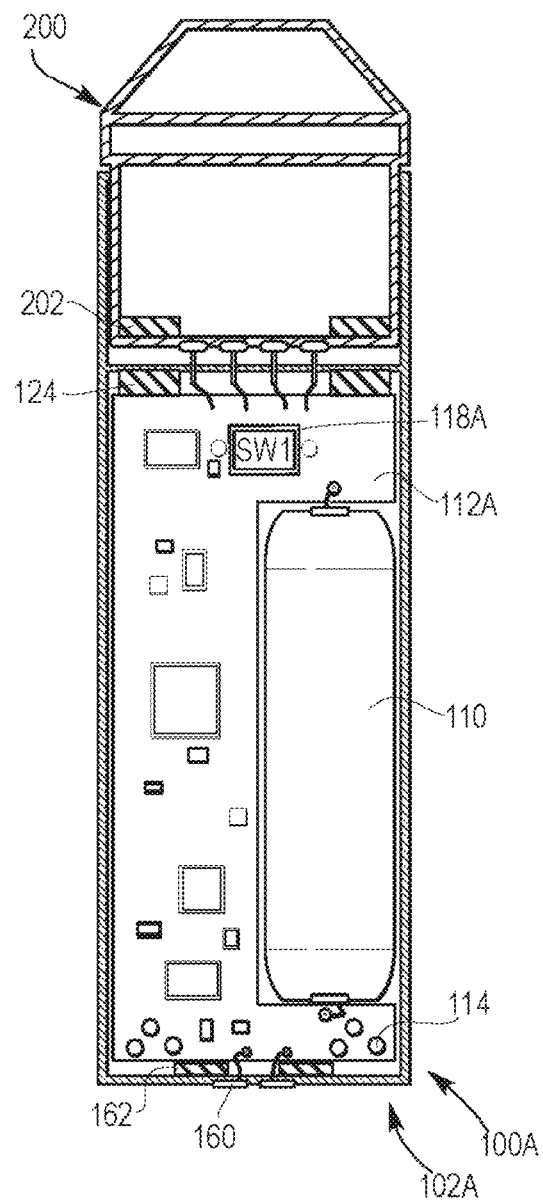
FIG. 8 illustrates a front view of an embodiment of an electronic cigarette, in accordance with the disclosure, comprising another embodiment of a battery portion with the outer shell of the second embodiment battery portion shown transparently so as to illustrate the inner components of the electronic cigarette.
Figure 9:
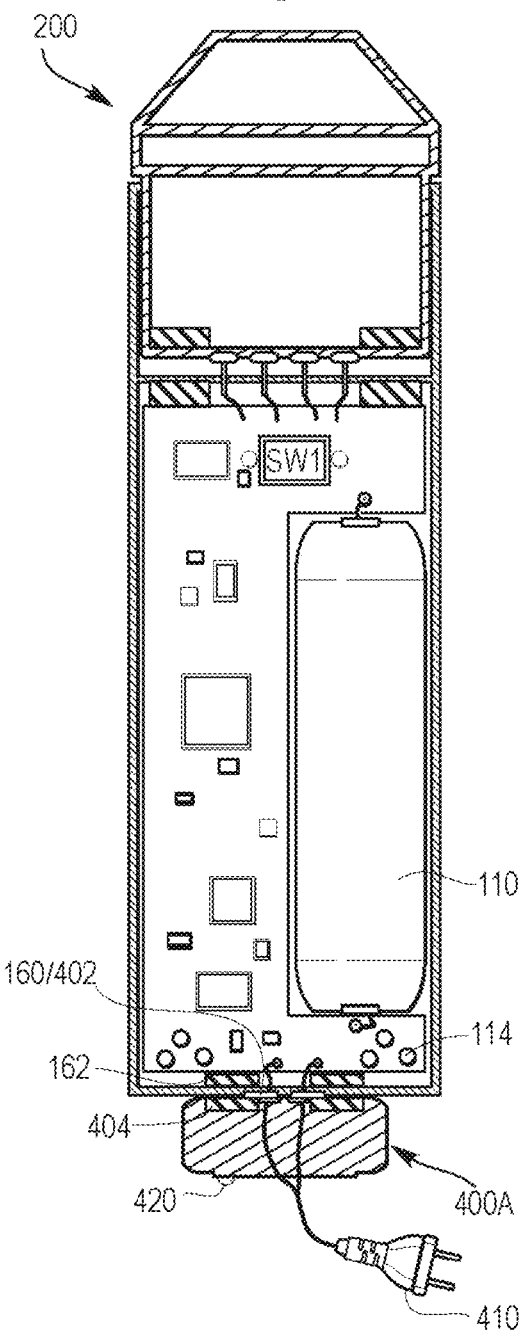
FIG. 9 illustrates a front view of the electronic cigarette of FIG. 8 with a charger attached, with the outer shell of another embodiment battery portion shown transparently so as to illustrate the inner components of the electronic cigarette.

FIGS. 8 and 9 illustrate an additional embodiment of an electronic cigarette 10 having a battery portion 100A for receiving a cartomizer such as cartomizer 200 or cartomizer 200B. PCB 112 may operate to perform a variety of functions including, such vaporization temperature control or regulation, voltage boost, accelerometer, or various drivers for controlling LED functioning. One or more LED indicators 114 may be provided and, in one embodiment, a set of three LED lights of variable colors are provided proximate to battery end 102A of the battery portion 100A. Magnets 124/202 may be provided in order to retain cartomizer 200 within cartomizer chamber 108. A switch 118A may be provided in order to manually activate or otherwise control electronic cigarette 10.

A battery charger 400A, having charging contacts 402, may be attached or connected to charging contacts 160 provided on outer shell 106, or otherwise exposable to the environment. In one embodiment, charging contacts 160 are positioned at or proximate to battery end 102A. Charging contacts 160, 402 may include a first positive contact and a second negative contact. In order to secure charging contacts 160 against corresponding charging contacts 402 of charger 400A, one or more magnets 162 may be provided proximate to charging contacts 160. Magnets 162 may then be capable of engaging with charger magnets 404 provided on portion of charger 400A such that magnets 162, 404 are adjacent to each other when contacts 160, 402 are contacting one another. In order to ensure the proper alignment of contacts 160, 402, two magnets 162 may be provided with opposed polarities, and two charger magnets 404 may be provided with opposed polarities. These opposed polarities may ensure proper orientation of charger 400A when it is connected to battery portion 100A. In some embodiments, battery portion magnet(s) 162 may operate to magnetically attract and connect a metallic charger surface 404, or charger magnets 404 may operate to magnetically attract and connect a metallic battery surface 162, each of these embodiments thereby operating to magnetically couple charger 400 with battery portion 100. An indicator light 420, which may be an LED, may be provided to indicate a charging status of battery 110. A charging extension 410 may be provided so as to connect charger 400A to a power source or, alternatively, a power source may be internally provided within charger 400A. Charging extension 410 may be an AC wall adapter to USB and USB cord to magnetic plug. Any charger 400 of the disclosure may contain OverVoltage and OverCurrent protection in order to prevent over charging of battery 110 thereby assuring long battery life and in order to reduce the likelihood of battery 110 overheating. In one embodiment, charger 400 is rated at approximately 1000 mA current, which for some embodiments will equate to approximately two hours of battery life. The battery life will vary depending on battery selection and number of batteries 110 used in a given embodiment.

Figure 10:
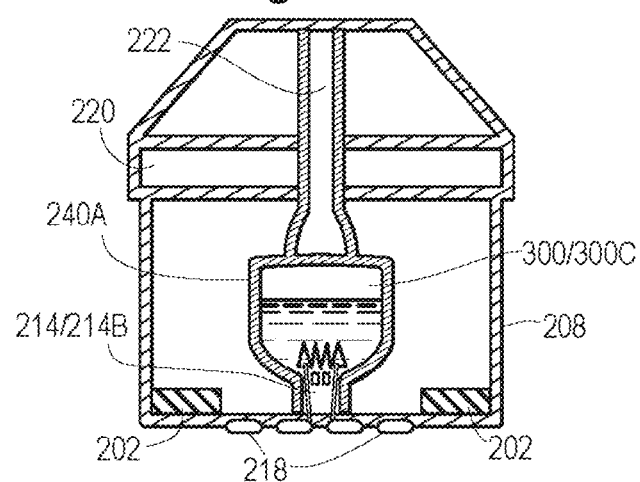
FIG. 10 illustrates a front cross sectional view of an embodiment of a cartomizer in accordance with the disclosure.

Referring now to FIG. 10, an embodiment for a cartomizer 200C is provided for holding a vaporizable substance 300. Cartomizer 200C may be used as an alternative cartomizer to 200/200B cartomizers, for example. Vaporizable substance 300 in cartomizer 200C may be a wax, oil or gel 300C. In cartomizer 200C, heating element 214 may be provided at the base of a basin 214B, which may or may not be removable from cartomizer body 208. Basin 214B may be dimensioned to hold wax, oil or gel 300C while heating element 214 may elevate the temperature within basin 214B to a vaporization temperature range, as controlled by PCB 112. Once the wax, oil or gel 300C is vaporized, a user may inhale the vapor through an inhalation tube 222 and out through mouthpiece 220. In some embodiments, mouthpiece 220 is removable through a friction fit, threaded connection, or any other known or to be developed connection means. One or more O-ring seals may also be provided proximate to the mouthpiece to ensure a fluid tight connection between mouthpiece 220 and cartomizer body 208.

Figure 11:
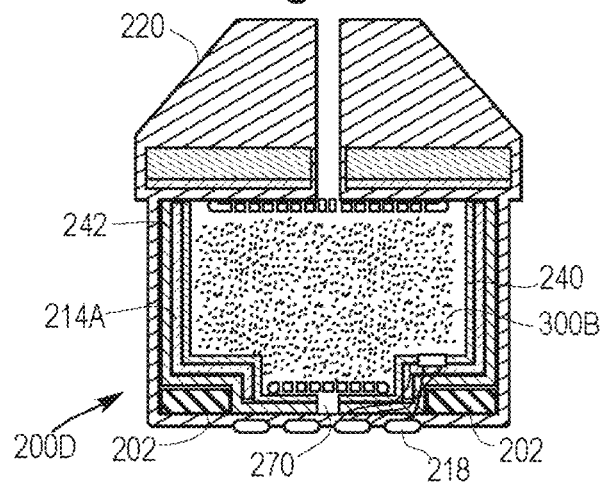
FIG. 11 illustrates a front view of an embodiment of a cartomizer in accordance with the disclosure.

FIG. 11 shows an additional embodiment of a cartomizer 200D for holding a dry vaporizable substance 300B. Cartomizer 200D may be used as an alternative cartomizer to 200/200B cartomizers, for example. Dry substance 300B may be held in a removable liner or container 240. Cartomizer 200D may also include heating element 214A and insulation material 242, each of which may be similarly provided and oriented as previously described with respect to cartomizer 200B. An air flow hole or aperture 270 may be provided at the base of cartomizer 200D. This airflow hole 270 may be provided off plane or misaligned with respect to electrical contacts 218. Airflow hole 270 may align with a hole between chamber 108 and battery portion 100A, which may house a fan 190 as described below. A temperature sensor 260 may also be included.

Figure 12:
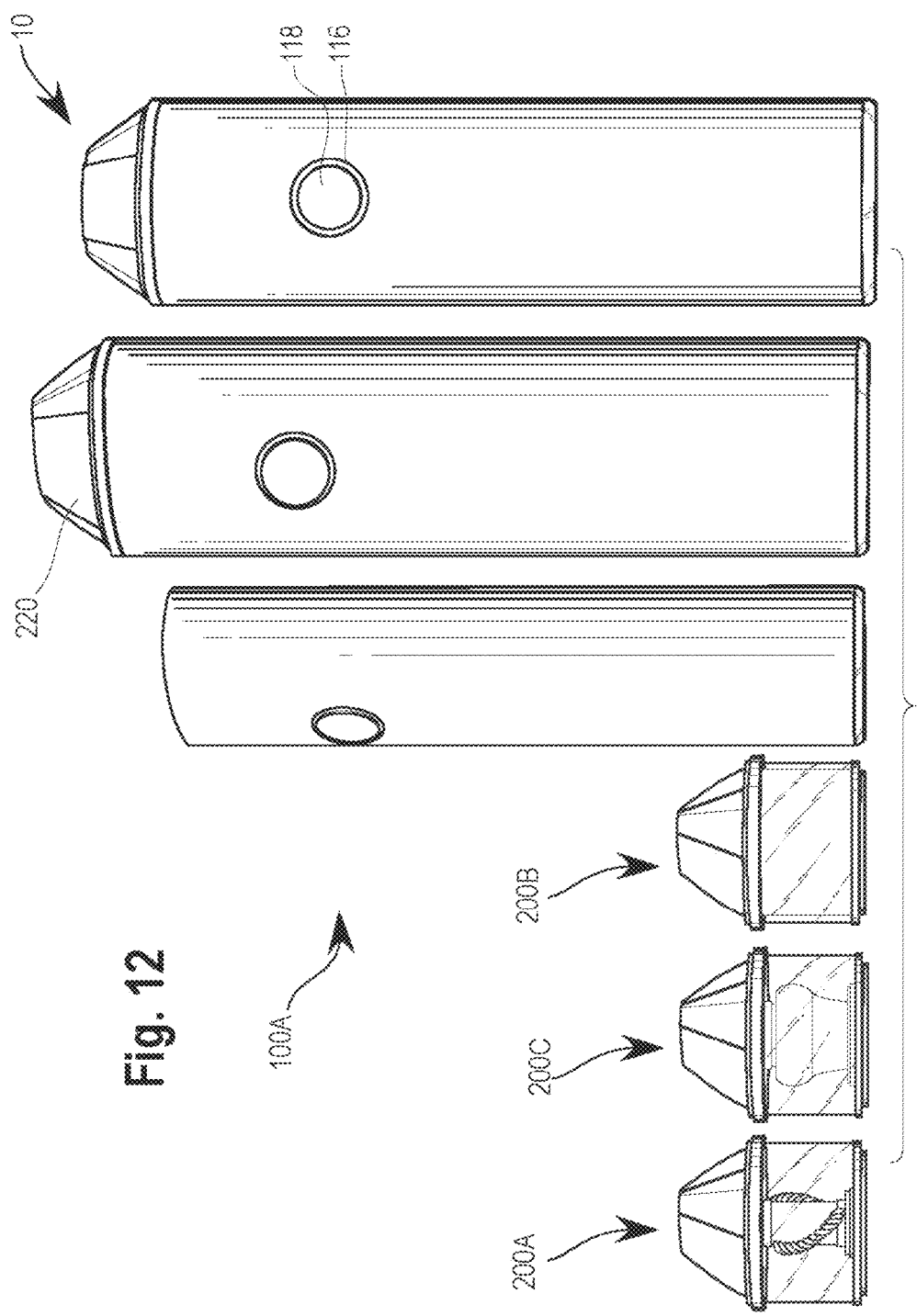
FIG. 12 illustrates embodiments of electronic cigarettes comprising the second battery portion of FIGS. 8-9 and the cartomizers of FIGS. 8-10.

FIG. 12 further illustrates the embodiments of an electronic cigarette 10 provided in FIGS. 9-11 in accordance with the disclosure.

Figure 15:
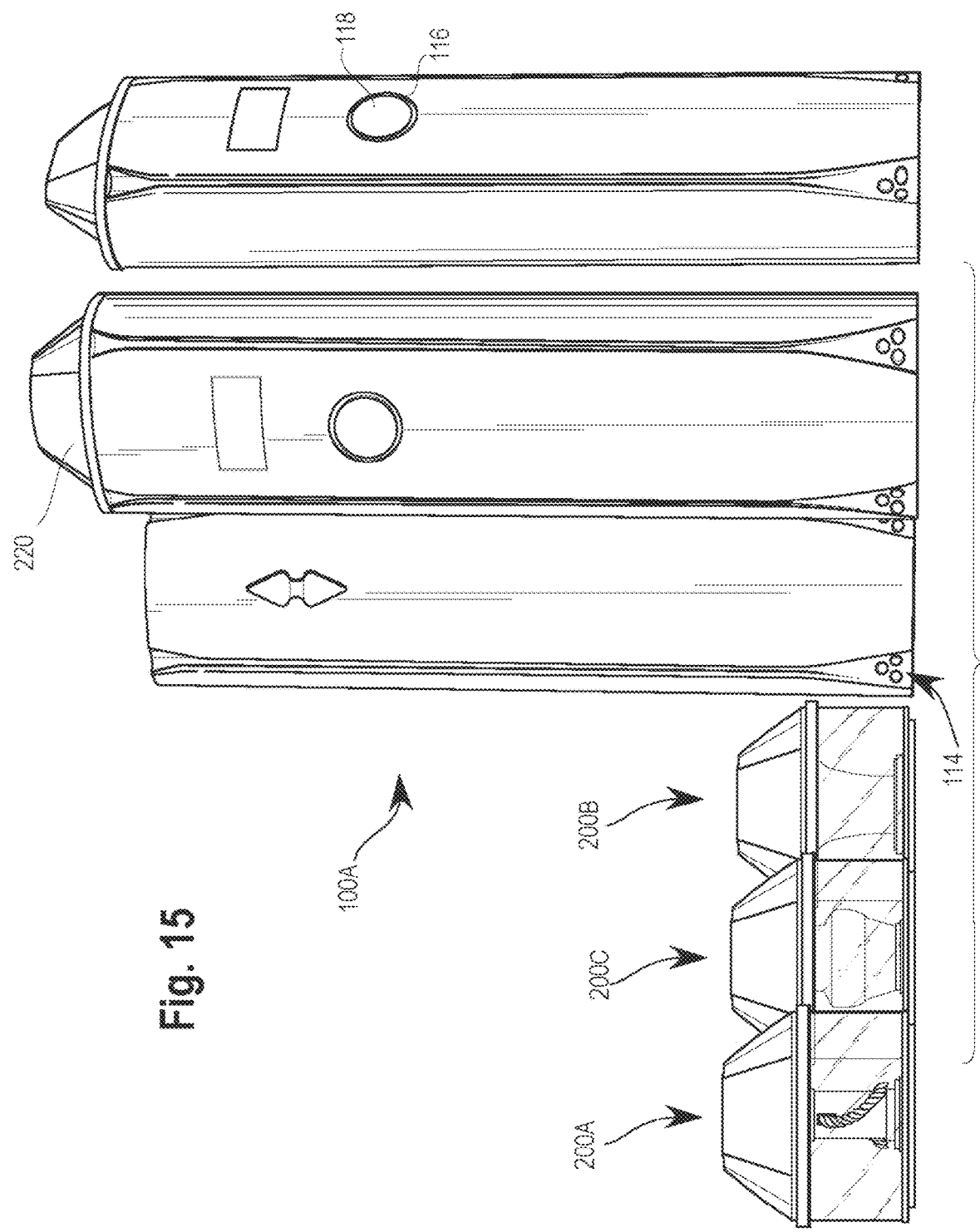
FIG. 15 illustrates embodiments of the electronic cigarette of FIGS. 13-14 in accordance with the disclosure.

Referring now to FIG. 13, an embodiment of an electronic cigarette 10 including a battery portion 100B is provided. PCB 112 may include a microcontroller, voltage boost integrated circuit, accelerometer, and a Fan control circuitry. A fan 190, including blades and a motor, may be provided internally in battery segment 110 of battery portion 100B. Fan 190 may operate to facilitate air flow from external battery portion 100B, such as through one or more holes 152 provided in outer shell 106, through battery segment 110 and into cartomizer thereby establishing an air flow for inhalation in accordance with the disclosure. In some embodiments, fan 190 has a reversible operation in order to "clear" the air flow path in the event debris or excess vapor is caught in the air flow path. PCB 112 may also include one or more switches that, for instance, may be provided beneath control buttons, such as that exemplified in FIG. 15). PCB 112 may also include one or more LED's for these and other similar switch lights. PCB 112 may also operate to display a status message on an LED screen, which may be provided on outer shell 106 (e.g., as shown in FIG. 15). A status message may, for example, include messages to indicate a status of the electronic cigarette 10, such as when the cigarette 10 is activated, charging, or has reached a vaporization temperature. An LED screen may also display warning or error messages, for instance a danger message when a critical temperature has been detected by a sensor. Further, as illustrated in FIG. 14. In some embodiments, PCB 112 may operate to recognize the cartomizer 200/200A/200B/200C inserted into chamber 108, and in order to identify the vaporizable substance 300 included in cartomizer 200. For instance, PCB 112 may communicate with sensor 260 in cartomizer 200 in order to identify both the type and amount of vaporizable substance 300 within cartomizer 200. This identification may be included in the status message displayable on the LED screen on outer shell 106. Charger 400A may be utilized for charging battery 110 in battery portion 100C. It should be understood and appreciated that, in some embodiments, charger 400A may be inserted into chamber 108 of battery portions 100A/100B in addition to connection of charger 400A as described herein. It should be further understood and appreciated that in embodiments where charger 400/400A is coupled with battery portion 100 at a position other than where cartomizer 200 is connected, such as embodiments where charger 400A is coupled at or proximate to first end 102A, electronic cigarette 10 may operate with a pass through function, namely the ability to operate electronic cigarette 10 while the unit is charging from charger 400A.

FIG. 15 further illustrates the embodiments of an electronic cigarette 10 provided in FIGS. 13-14 in accordance with the disclosure.

Certain charger embodiments for rechargeable vaporizers or electronic cigarettes disclosed hereinabove, for example in FIG. 3, employ electrical contacts between the charger and the cartomizer portion's electrical connector. Under these circumstances, the cartomizer portion is first removed from the chamber to expose the electrical connector and thereafter a charger with compatible electrical contacts is inserted into the chamber. The invention contemplates other types and locations of connectors on the vaporizer and charger. Accordingly, in certain embodiments, the present invention provides a charger 400 for charging a vaporizer or electronic cigarette having charging contacts attached essentially transversely to its outer shell at an end distal to the cartomizer receiving portion and proximate to its battery portion. One such embodiment is shown in FIG. 14. In some of these embodiments where the cartomizer portion is not removed from the vaporizer to expose the electrical connector, the charging contacts are incorporated into the device such that the vaporizer or electronic cigarette may be operated in its typical fashion during the recharging of the battery ("pass-through" charging).

Figure 16:
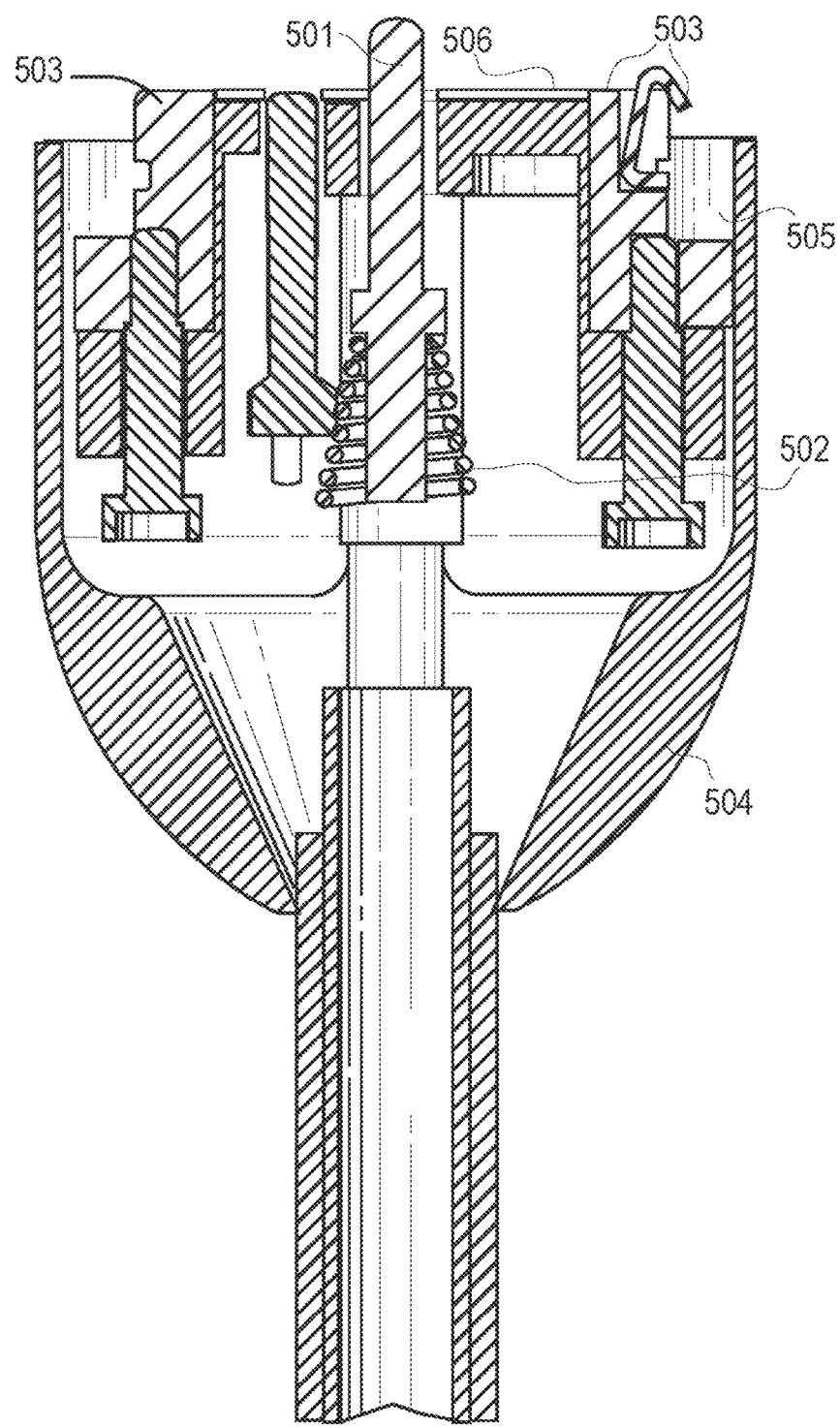
FIG. 16 illustrates a longitudinal cross sectional view of an embodiment of charger contacts on a power cord of a vaporizer or electronic cigarette charger of the present invention.
Figure 17:
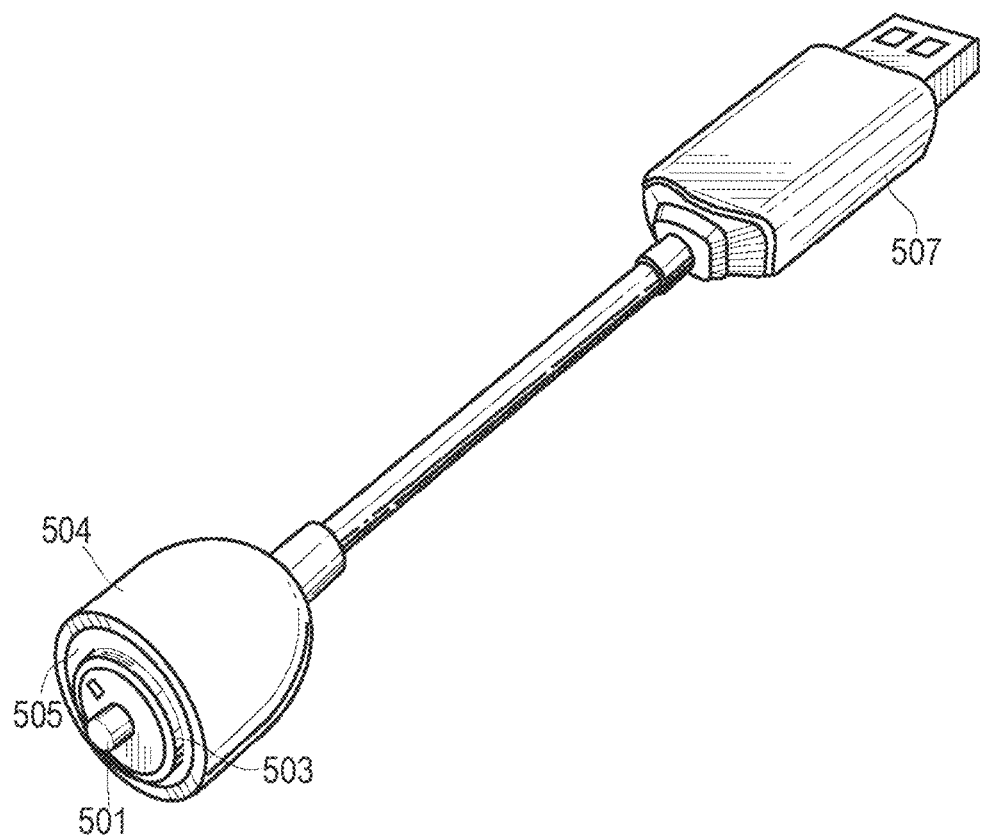
FIG. 17 illustrates a perspective view of an embodiment of charger contacts on a power cord of a vaporizer or electronic cigarette charger of the present invention.

Still other embodiments for chargers and rechargeable vaporizers or electronic cigarettes are illustrated in FIGS. 16, 17, 18, 19, and 20. For example, FIG. 16 depicts aspects of the portion of the charger that connects with the vaporizer during the charging operation. In this example, the positive connection to the vaporizer's charging contacts is facilitated through the use of a spring-loaded pogo pin (see 501 and 502). The negative connection pin (503) or other negative connection is isolated from the pogo pin by an insulator 506 to isolate the positive and negative connections from each other. At the contacts insulator surface such that it is isolated from electrical connections 501 and 503 is a wiper contact that is capable of powering a LED charging indicator light. In some instances the exterior housing 504 for the charger is at least in part, translucent or transparent, so that the indicator lamp can be readily observed. To maintain readily removable connectivity with the vaporizer, a magnet 505 is provided, and is typically in proximity to the outer edges of the charger's charging contacts and optionally takes the form of a ring disposed in substantially concentric fashion about the assembly containing the electrical contacts and insulation. The charger is generally held in the correct position for charging by magnetic attraction to the vaporizer's charging contacts. The magnetic attraction strength is such that the charger can be easily detached by just pulling on the charger. This level of attractive force may also allow the charger to break away if it is pulled too far away from the battery portion of the vaporizer so that no significant damage will occur to the vaporizer or the charger. Other aspects of the charger include one or more of support pieces and/or fixing screws, for example. The materials employed in the construction of the charger would be readily understood by the ordinarily skilled artisan once equipped with the teachings of the present invention. Any material that conducts electricity will generally be acceptable where transfer of electricity to charge the battery is required. Similarly, where insulation is a necessary property for normal operation, electrically non-conductive materials are typically acceptable. FIG. 17 illustrating a perspective drawing of a charger that employs a USB terminus connection 507 as a source of power for the charging operation. At the end distal to the USB terminus are the charger's charging contacts for the vaporizer or electronic cigarette, including a pogo pin-type positive connection 501, an insulator 506, a negative connection 503, a magnet 505 and a housing 504.

Figure 18:
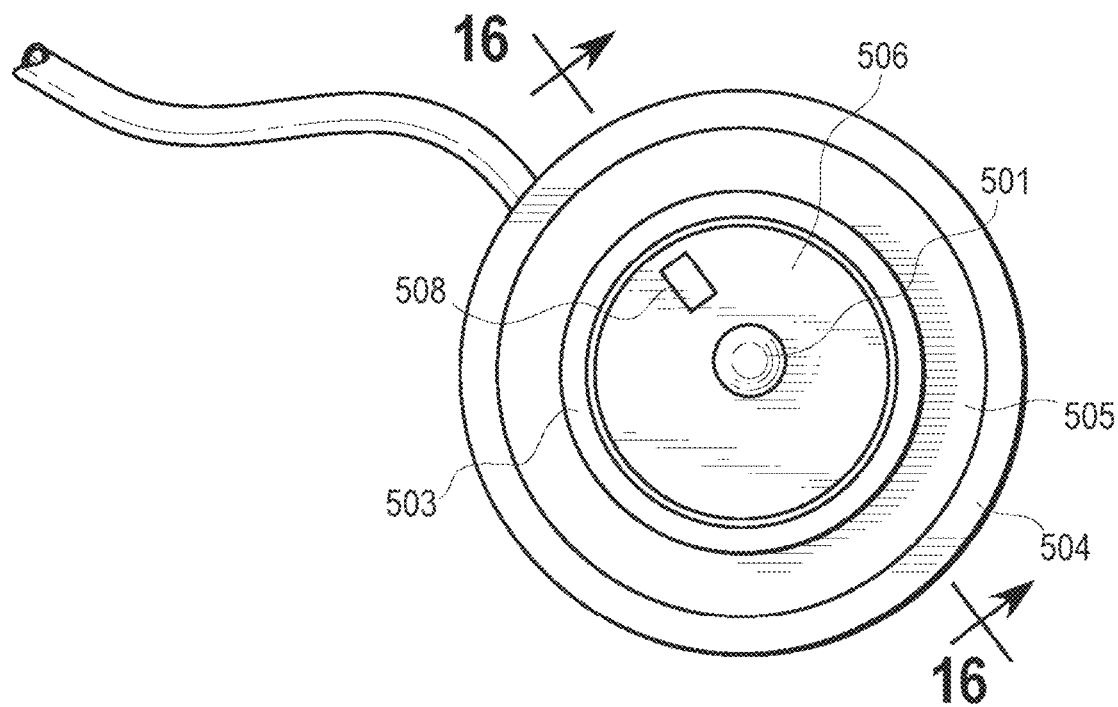
FIG. 18 illustrates a lateral view of an embodiment of charger contacts on a power cord of a vaporizer or electronic cigarette charger of the present invention.

FIG. 18 shows an alternate end on view of a charger's electrical contacts region, depicting a housing 504, magnet 505, negative connection 503, wiper contact 508 for an optional LED-type charging indicator light disposed on the housing, pogo pin-type positive connection 501, and insulator 506.

Figure 19:
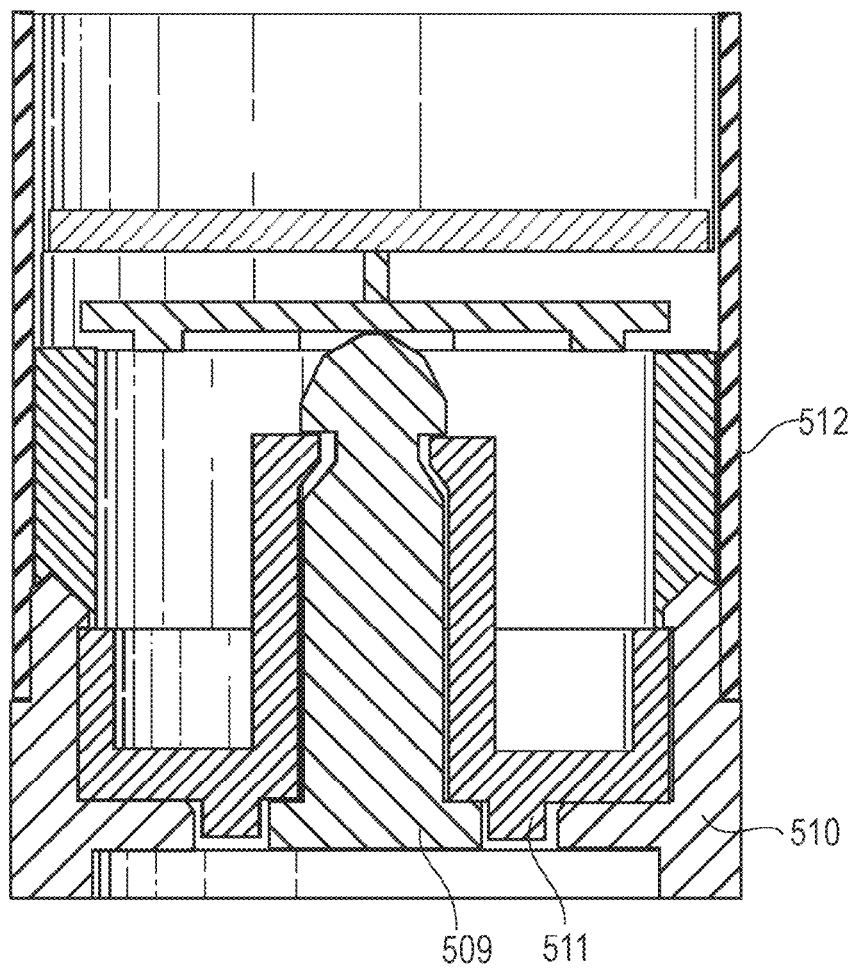
FIG. 19 illustrates a longitudinal cross sectional view of an embodiment of charger contacts of a vaporizer or electronic cigarette for connecting with a vaporizer or electronic cigarette charger of the present invention.

FIG. 19 illustrates a partial longitudinal cross section view of an embodiment of the vaporizer's electrical connector attached essentially transversely to its outer shell 512 at an end distal to the cartomizer receiving portion and proximate to its battery portion, which may be contacted with the chargers contacts illustrated in FIG. 18. FIG. 19 shows an arrangement of components for an embodiment of present invention's electrical connector including a positive contact 509, negative contact 510, and insulation 511.

Figure 20:
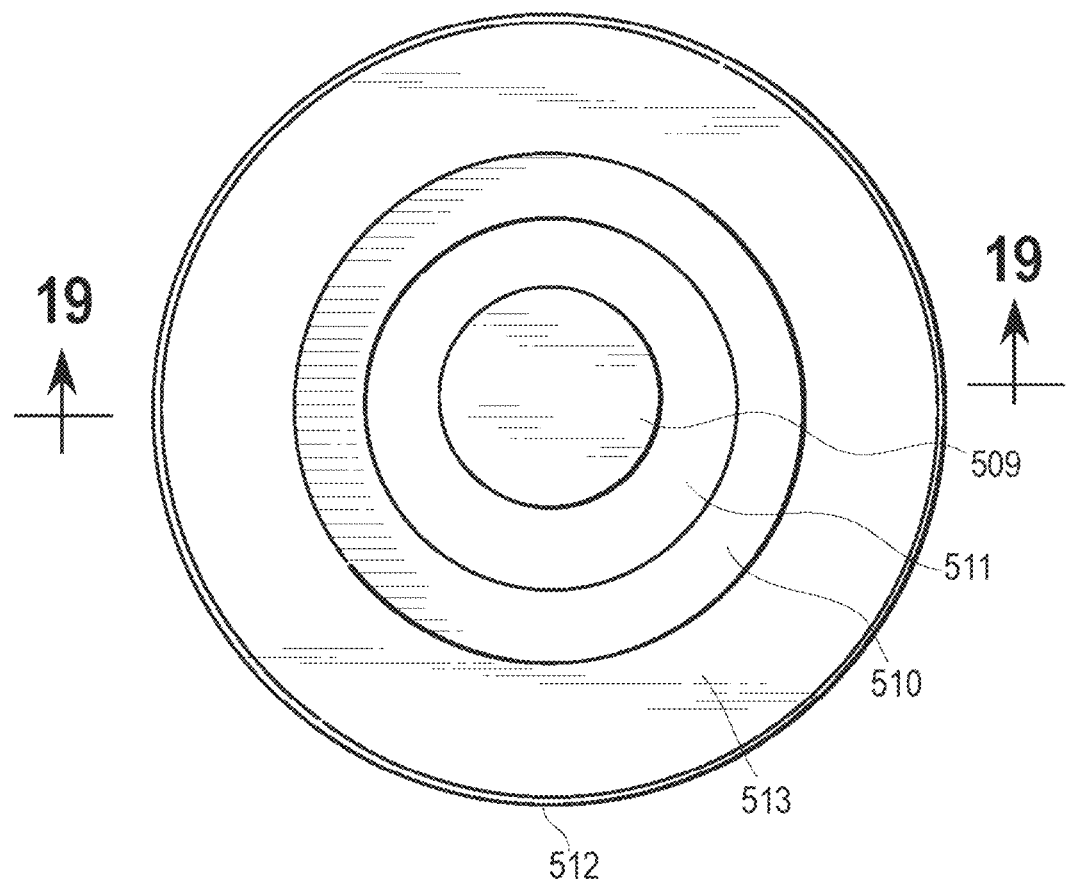
FIG. 20 illustrates a lateral cross sectional view of an embodiment of charger contacts on a vaporizer or electronic cigarette for connecting with a vaporizer or electronic cigarette charger of the present invention.

An alternative vaporizer electrical connector compatible with the charger shown in FIG. 18 is shown in FIG. 20 in an end on view. In this view, the positive contact 509 forms an innermost circle, surrounded by concentric circles of independently varying dimensions including an insulator 511, a negative contact 510, a magnet 513 and outer shell 512. In certain embodiments 513 may be a magnet or a magnetic material. In embodiments where 513 is a magnetic material, it is preferably magnetic metal, more preferably a ferromagnetic metal. The magnetic attraction between 513 and the magnet in the charger contacts is strong enough to hold the charger contacts and vaporizer charging contacts sufficiently so that the battery may be recharged. In certain preferred embodiments, the attraction is sufficiently strong to maintain the charger/vaporizer connection, but weak enough to be disconnected without substantial damage to the charger or the vaporizer.

Figure 21:
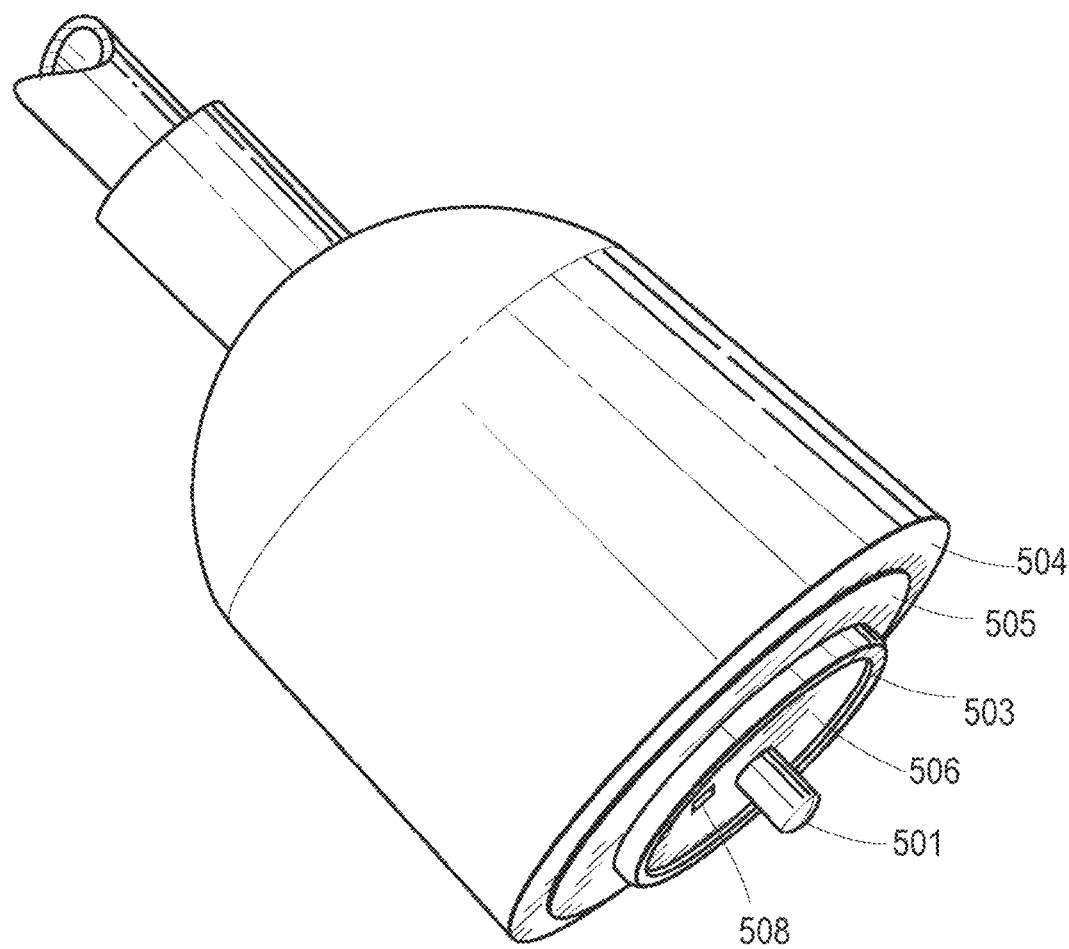
FIG. 21 illustrates a perspective view of an embodiment of charger contacts on a power cord of a vaporizer or electronic cigarette charger of the present invention.

FIG. 21 shows a perspective side on view of the FIG. 18 charger's electrical contacts region depicting a housing (504), magnet (505), negative connection (503), wiper contact (508), pogo pin-type positive connection (501), and insulator (506).

Figure 22:
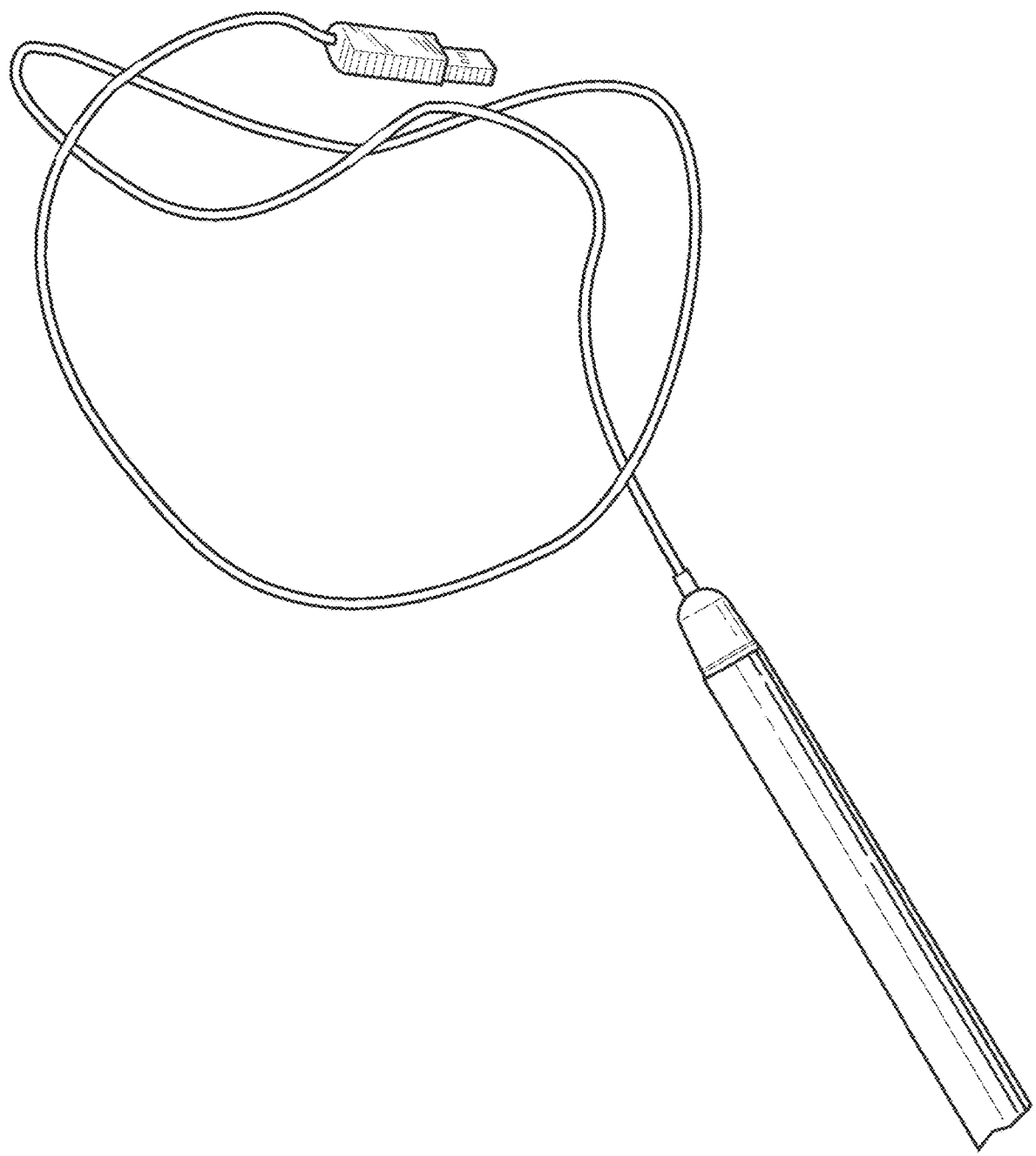
FIG. 22 illustrates a side view of an embodiment of a charger of the present invention in contact with charger contacts of a vaporizer or electronic cigarette for charging a vaporizer or electronic cigarette battery.

FIG. 22 shows the charger of FIG. 18 connected for recharging to the electrical connector of the vaporizer compatible with the charger shown in FIG. 20.

Vaporizer or electronic cigarette charger kits useful in, for example, the recharging of batteries used to power the vaporization process in such devices, are also within the ambit of the present invention. These kits typically include one or more chargers of the present invention, or alternatively a charger with multiple interchangeable power connectors (e.g., wall plug and USB connector). Such kits may further include, if desired, one or more of various compatible vaporizers or electronic cigarettes, their components, such as for example, one or more interchangeable cartomizers, cartomizer refills, etc., as will be readily apparent to those skilled in the art. Instructions, either as inserts or as labels, indicating quantities of the components contained in the kit, guidelines for operation or use, and/or guidelines for connecting any of the components and/or refilling the cartomizers, may also be included in the kit.

In accordance with certain embodiments of the present invention, there are provided methods which comprise contacting a charger of the present invention with a compatible vaporizer or electronic cigarette for a time and under conditions effective to recharge a rechargeable battery contained within said vaporizer or electronic cigarette sufficient to repower vaporizer or electronic cigarette for its continued use.

As will be understood by the ordinarily skilled artisan equipped with the disclosure herein, electrical contacts compatible with the charger must be provided for on or within the vaporizer or electronic cigarette.

The descriptions set forth above are meant to be illustrative and not limiting, and persons of skill in the art will recognize that various common and known deviations from the above described structures are considered to be within the scope of the disclosed concepts described herein.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

LIST OF REFERENCES

10 Electronic Cigarette
100 Battery Portion
100A Battery Portion
100B Battery Portion
102 Battery Housing Segment
102A First end of Battery Portion
104 Cartomizer Receiving Segment
104A Second end of Battery Portion
106 Shell
108 Cartomizer Chamber
110 Battery
112 PCB
112A PCB
114 Indicator
116 Ring Indicator
118 Button
118A Switch
120 Electrical Connector
122 Pin
124 Magnet
126 Protrusion
130 Window
152 Hole
160 Charging Contact
162 Magnet
190 Fan
200 Cartomizer
200A Cartomizer
200B Cartomizer
200C Cartomizer
202 Magnet
204 Groove
208 Body
210 Insertion End
212 Mouthpiece End
214 Heating Element
214A Heating Element
214B Basin
216 Wick
218 Electrical Contact
220 Mouthpiece
222 Inhalation Tube
224 Threading
226 Bushing
228 Colored Ring
240 Container
242 Insulating Material
250 Screen
252 Hole
260 Sensor
262 Cartomizer PCB
300 Vaporizable Substance
300A Vaporizable Fluid
300B Vaporizable Dry Substance
300C Vaporizable Wax
400 Charger
400A Charger
402 Electrical Contact
404 Magnet
410 Plug
420 Light
501 pogo pin
502 spring
503 negative connection pin
504 exterior housing
505 magnet
506 insulator
507 USB terminus connection
508 wiper contact
509 positive contact
510 negative contact
511 insulation
512 outer shell
513 magnet or magnetic metal

The invention claimed is:

1. A vaporizer comprising:
a battery portion having a battery portion first end and a battery portion second end opposite the battery portion first end, the battery portion comprising:
a battery housing segment proximate the battery portion first end, the battery housing segment housing a battery;
a cartomizer receiving segment proximate the battery portion second end, the cartomizer receiving segment defining a chamber having an opening at a chamber insertion end distal to the battery housing segment and a chamber base end opposite the chamber insertion end, the chamber base end proximate the battery housing segment;
a battery electrical contact proximate the chamber base end, the battery electrical contact configured to receive an electrical current from the battery; and
an outer shell commonly shared by the battery housing segment and the cartomizer receiving segment; and
a cartomizer having a cartomizer insertion end configured for insertion into the opening at the chamber insertion end, the cartomizer comprising:
a cartomizer body;
a basin within the cartomizer body, the basin configured to hold a vaporizable liquid substance;
a heating element proximate the basin and positioned such that the entire heating element is disposed between the opening at the chamber insertion end and the chamber base end when the cartomizer is inserted into the chamber such that the outer shell protects the heating element; and
a wicking element configured to deliver the vaporizable liquid to the heating element; and
a cartomizer electrical contact disposed proximate the cartomizer insertion end, the cartomizer electrical contact configured to contact the battery electrical contact to direct the electrical current from the battery electrical contact to the heating element to heat the vaporizable substance.

2. The vaporizer in accordance with claim 1, further comprising a mouthpiece in fluid communication with the basin, the mouthpiece extending outside the chamber when the cartomizer is inserted into the chamber.

3. The vaporizer in accordance with claim 1, further comprising one or more electrical circuits configured to control one or more functions of the vaporizer.

4. The vaporizer in accordance with claim 3, wherein the one or more electrical circuits are connected with the battery electrical contact and/or the cartomizer electrical contact.

5. The vaporizer in accordance with claim 3, wherein the one or more electrical circuits are configured to switch the heating element between an active state and an inactive state.

6. The vaporizer in accordance with claim 3, wherein the one or more electrical circuits configured to control the vaporizer are operable to switch the heating element between a conduction heating and a convection heating.

7. The vaporizer in accordance with claim 3, wherein the one or more electrical circuits comprise at least one of an integrated circuit, a printed circuit board (PCB), and a micro control unit.

8. The vaporizer in accordance with claim 3, further comprising an accelerometer operable to detect tilting or changes in orientation of the battery portion.

9. The vaporizer in accordance with claim 8, wherein the one or more electrical circuits are configured to react to a shift in the orientation of the battery portion detected by the accelerometer.

10. The vaporizer in accordance with claim 8, wherein the one or more electrical circuits are configured to activate the vaporizer when the accelerometer detects a shaking or an inverting of the vaporizer.

11. The vaporizer in accordance with claim 1, wherein the battery portion further comprises a connection mechanism to secure and align the cartomizer within the chamber.

12. The vaporizer in accordance with claim 11, wherein the connection mechanism comprises a magnet in or proximate to the chamber.

13. The vaporizer in accordance with claim 1, wherein the outer shell is formed of metal.

14. The vaporizer in accordance with claim 1, further comprising a window formed in the outer shell, the window provided on or proximate to the chamber to permit viewing of the cartomizer when the cartomizer is inserted into the chamber.

15. The vaporizer in accordance with claim 1, wherein the cartomizer contains the vaporizable substance, and wherein the vaporizable substance comprises a liquid comprising nicotine.

16. The vaporizer in accordance with claim 1, wherein the battery portion comprises an indicator operable to indicate a status of the vaporizer.

17. The vaporizer in accordance with claim 16, wherein the indicator comprises a light emitting diode.

18. The vaporizer in accordance with claim 16, wherein the status comprises one or more of power remaining in the battery, a charge state of the battery, or an activation state of the vaporizer.

19. The vaporizer in accordance with claim 16, wherein the status comprises a status change.

20. The vaporizer in accordance with claim 19, wherein the status change comprises the insertion of the cartomizer into the chamber.

21. The vaporizer in accordance with claim 1, wherein the battery electrical contact comprises a pogo pin.

22. The vaporizer in accordance with claim 21, wherein the pogo pin extends into the chamber when the cartomizer is not inserted into the chamber, and wherein the pogo pin is contacted and at least partially compressed when the cartomizer is inserted into the chamber.

23. The vaporizer in accordance with claim 22, wherein the pogo pin that is pressed against the cartomizer electrical contact establishes an electrical connection between cartomizer electrical circuitry and the battery electrical contact when the cartomizer is inserted into the chamber.

24. A vaporizer comprising:
a battery portion having a battery portion first end and a battery portion second end opposite the battery portion first end, the battery portion comprising:
a battery housing segment proximate the battery portion first end, the battery housing segment housing a battery;
a cartomizer receiving segment proximate the battery portion second end, the cartomizer receiving segment defining a chamber having an opening at a chamber insertion end, the chamber insertion end being distal to the battery housing segment, the chamber also having a chamber base end opposite the chamber insertion end and proximate the battery housing segment;
a plurality of battery electrical contacts proximate the chamber base end, the plurality of battery electrical contacts comprising a plurality of contact surfaces configured to receive an electrical current from the battery; and
an outer shell; and
a cartomizer having a cartomizer insertion end configured for insertion into the opening at the chamber insertion end, the cartomizer comprising:
a cartomizer body;
a basin within the cartomizer body, the basin configured to hold a vaporizable liquid substance;
a heating element, wherein the entire heating element is disposed between the opening and the chamber base end when the cartomizer is inserted into the chamber such that the outer shell protects the heating element; and
a wicking element configured to deliver the vaporizable liquid substance to the heating element; and a plurality of cartomizer electrical contacts disposed and configured to contact the plurality of battery electrical contacts to direct the electrical current from the plurality of battery electrical contacts to the heating element to heat the vaporizable substance.

25. The vaporizer in accordance with claim 24, further comprising one or more electrical circuits configured to control one or more functions of the vaporizer.

26. The vaporizer in accordance with claim 25, wherein the one or more electrical circuits are connected with the plurality of battery electrical contacts and/or the plurality of cartomizer electrical contacts.

27. The vaporizer in accordance with claim 25, wherein the one or more electrical circuits are configured to switch the heating element between an active state and an inactive state.

28. A vaporizer comprising:
a battery portion having a battery portion first end and a battery portion second end opposite the battery portion first end, the battery portion comprising:
a battery housing segment for housing a battery;

a cartomizer receiving segment proximate the battery housing segment, the cartomizer receiving segment defining a chamber, the chamber having an opening at a chamber insertion end and a chamber base end that is opposite the chamber insertion end and proximate to the battery housing segment, the chamber base end comprising a plurality of battery electrical contacts configured to receive an electrical current from the battery, the plurality of battery electrical contacts being positioned in a line; and an outer shell containing the battery housing segment and the cartomizer receiving segment; and a cartomizer having a cartomizer body configured for insertion into the opening at the chamber insertion end, the cartomizer body having a mouthpiece end and a cartomizer insertion end, the cartomizer comprising:

a basin within the cartomizer body, the basin configured to hold a vaporizable liquid substance;

a heating element proximate the basin, wherein the entire heating element is disposed between the opening at the chamber insertion end and the chamber base end when the cartomizer is inserted into the chamber such that the outer shell protects the heating element;

a wicking element configured to deliver the vaporizable liquid substance to the heating element; and a mouthpiece disposed at the mouthpiece end; and a plurality of cartomizer electrical contacts proximate the cartomizer insertion end, the plurality of cartomizer electrical contacts configured to align and to contact the plurality of battery electrical contacts to direct the electrical current to the heating element to heat the vaporizable substance.

29. The vaporizer of claim 1, wherein the basin comprises a ceramic material.

30. The vaporizer of claim 1, wherein the heating element is disposed at a base of the basin and proximate to the cartomizer insertion end, the heating element configured to heat the vaporizable substance within the basin.

* * * * *